(12) United States Patent
Lean et al.

(10) Patent No.: US 7,309,410 B2
(45) Date of Patent: *Dec. 18, 2007

(54) TRAVELING WAVE GRIDS AND ALGORITHMS FOR BIOMOLECULE SEPARATION, TRANSPORT AND FOCUSING

(75) Inventors: Meng H. Lean, Santa Clara, CA (US); Jeng Ping Lu, San Jose, CA (US); Jackson Ho, Palo Alto, CA (US); Chinwen Shih, Santa Clara, CA (US); Armin R. Völkel, Mountain View, CA (US); Huangpin Ben Hsieh, Mountain View, CA (US); Jurgen Daniel, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 785 days.

This patent is subject to a terminal disclaimer.

(21) Appl. No.: 10/727,301

(22) Filed: Dec. 3, 2003

(65) Prior Publication Data
US 2005/0123930 A1   Jun. 9, 2005

(51) Int. Cl.
*G01N 27/453* (2006.01)
(52) U.S. Cl. ...................... 204/643; 204/609
(58) Field of Classification Search ................ 204/547, 204/643, 609, 458
See application file for complete search history.

(56) References Cited

U.S. PATENT DOCUMENTS

| | | | |
|---|---|---|---|
| 4,473,452 A | 9/1984 | Cantor et al. |
| 4,647,179 A | 3/1987 | Schmidlin |
| 4,737,251 A | 4/1988 | Carle et al. |
| 5,208,458 A | 5/1993 | Busch et al. |
| 5,534,121 A | 7/1996 | Merrick et al. |
| 5,653,859 A | 8/1997 | Parton et al. |
| 5,837,116 A | 11/1998 | Harrington et al. |
| 6,193,866 B1 | 2/2001 | Bader et al. |
| 6,272,296 B1 | 8/2001 | Gartstein |
| 6,296,752 B1 | 10/2001 | McBride et al. |
| 6,358,752 B1 | 3/2002 | Durst et al. |

(Continued)

FOREIGN PATENT DOCUMENTS

DE   10223127   5/2002

(Continued)

OTHER PUBLICATIONS

Frénéa et al. (<< A Multilayer Microelectrode array for Particle separation by Dielectrophoresis, >> Micro Total Analysis systems 2002, vol. 1, 578-580, Y. Baba et al. (eds.)).*

(Continued)

*Primary Examiner*—Alex Noguerola
(74) *Attorney, Agent, or Firm*—Fay Sharpe LLP

(57) ABSTRACT

Various traveling wave grids and related systems are disclosed that are particularly beneficial for the separation, transport, and focusing of biomolecules or other charged species. An implementation of a vertically integrated traveling wave module is described which allows for scalability to arbitrary gel dimensions through tiling. In addition, several unique traveling wave algorithms are also described which when used in conjunction with the traveling wave grids, impart selective motion to biomolecules or other charged species.

24 Claims, 23 Drawing Sheets

U.S. PATENT DOCUMENTS

| | | | |
|---|---|---|---|
| 6,398,933 | B1 | 6/2002 | Scott |
| 6,499,831 | B2 | 12/2002 | Schmidlin |
| 7,156,970 | B2 * | 1/2007 | Lean et al. .................. 204/547 |
| 2001/0023825 | A1 | 9/2001 | Frumin et al. |
| 2002/0144895 | A1 | 10/2002 | Stern et al. |
| 2003/0015467 | A1 | 1/2003 | Johnston et al. |
| 2003/0027135 | A1 | 2/2003 | Ecker et al. |
| 2003/0034290 | A1 | 2/2003 | Tochikubo et al. |

FOREIGN PATENT DOCUMENTS

| | | |
|---|---|---|
| JP | 60242358 | 2/1985 |
| WO | WO 99/36357 | 7/1999 |
| WO | WP 00/73780 | 12/2000 |

OTHER PUBLICATIONS

British Berkefeld, James Filter, http://www.jamesfilter.com/, Jun. 23, 2003.

Filtros Ltd., *Filtros*, http//www.filtrosltd.com/, Jun. 23, 2003.

REI, http://www.rei.com/, Jun. 23, 2003.

Scott Rudge et al., Electroseparations (Electrophoresis), *Encyclopedia of Chemical Technology*, 4th Edition, vol. 9, pp. 356-376, date unknown.

O'Hara et al., *Ratcheting Electrophoresis Microchip (REM) for Programmable Transport and Separation of Macromolecules*, MEMS, Nov. 11-16, 2001, pp. 619-628, vol. 3, ASME, USA.

Dunphy et al., *Rapid Separation and Manipulation of DNA by a Ratcheting Electrophoresis Microchip (REM)*, Nov. 17-22, 2002, pp. 419-423, ASME, USA.

Proteome Systems, Products, Website, *Electrophorett$Q^3$*, 2002 at http://www.proteomesystems.com/product/product.asp-?ProductID=43 and http://www.proteomesystems.com/product/profile.asp?DocumentID=662.

ISC Buyers' Guide, Website, *Electrophoresis, 2D Gel*, 2002, at http://www.iscpubs.com/bg/us/prod/prod1991.html.

EMBL's Proteomics Visitor Facility, Website, 2D Gel Equipment, *Protean 2D Cells from Bio-Rad*, 2001, at http://.mann.embl-heidelberg.de/Visitor_Facility/PageLinks/Instrumentation/GelchamberMain.html, and *Protean IEF Cell from Bio-Rad*, at http://www.mann.embl-heidelberg.de/Visitor_Facility/PageLinks/Instrumentation/ECellMain.html.

James R. Jefferies,, *2D Gel Electrophoresis for Proteomics Tutorial*, pp. 1-24 at http://www.aber.ac.uk/parasitology/Proteome/Tut_2D.html (last tutorial update: Jan. 7, 2003).

The Scripps Research Institute, Website, *Proteomics Module*, 2003, pp. 1-3 at http://core-eye.scripps.edu/proteomics.htm.

2D Protocols, Website, *Analysis of Proteins Using Small Format 2D Gel Electrophoresis*, 2000, pp. 1-5, at http://www.abdn.ac.uk/~mmb023/protocol.htm.

Biowire.com, Website, *The Nucleus*, 2000-2002, pp. 1-4, at http:/www.biowire.com/nucleus/nucleus_1_3.jsp.

Bio-Rad Laboratories, Website, *Electrophoresis*, 2003, at http:www.bio-rad.com/B2B/BioRad/produict/br_category.jsp.

* cited by examiner

TRAVELING WAVE GRIDS AND ALGORITHMS FOR BIOMOLECULE SEPARATION, TRANSPORT AND FOCUSING

TECHNICAL FIELD

The present subject matter relates to the field of electrophoretic separation of molecules, and, more particularly, to their separation, transport, and focusing such as into narrow bands in gel electrophoresis. The present subject matter also relates to traveling wave algorithms for selectively transporting biomolecules in gel systems.

BACKGROUND

Electrophoresis is a separation technique most often applied to the analysis of biological or other polymeric samples. It has frequent application to analysis of proteins and DNA fragment mixtures. The high resolution of electrophoresis has made it a key tool in the advancement of biotechnology. Variations of this methodology are used for DNA sequencing, isolating active biological factors associated with diseases such as cystic fibrosis, sickle-cell anemia, myelomas, and leukemia, and establishing immunological reactions between samples on the basis of individual compounds. Electrophoresis is an extremely effective analytical tool because it does not affect a molecule's structure, and it is highly sensitive to small differences in molecular charge and mass.

Electrophoresis in a polymeric gel, such as a polyacrylamide gel or an agarose gel, adds two advantages to an electrophoretic system. First, the polymeric gel stabilizes the electrophoretic system against convective disturbances. Second, the polymeric gel provides a porous passageway through which the molecules must travel. Since larger molecules will travel more slowly through the passageways than smaller molecules, use of a polymeric gel permits the separation of molecules by molecular size.

One common electrophoretic procedure is to establish solutions having different pH values at each end of an electric field, with a gradient range of pH in between. At a certain pH, the isoelectric point of a molecule is obtained and the molecule carries no net charge. As the molecule crosses the pH gradient, it reaches an isoelectric point and is thereafter immobile in the electric field. Therefore, this electrophoresis procedure separates molecules according to their different isoelectric points.

More specifically, this procedure is referred to as isoelectric focusing (IEF) in which an electric field is applied to a molecule in a pH gradient to mobilize the molecule to a position in the pH gradient at which its net charge is zero, i.e., the isoelectric point of the molecule. It often is used to separate proteins in a mixture and as an aid in the characterization of biomolecules of unknown composition. Commercially available gradients may be utilized in isoelectric focusing which consist of multicharged ampholytes, with closely spaced isoelectric values and high conductivity, which partition into a pH gradient upon application of an electric field. The ampholytes are generally provided in a support matrix, such as a polyacrylamide gel.

Because protein samples are actually ampholytes, when samples are loaded onto the gel and a current is applied, the compounds migrate through the gel until they come to their isoelectric point where they reach a steady state. Isoelectric focusing takes a long time (from about 3 to 30 hours) to complete because sample compounds move more and more slowly as they approach the pH in the gel that corresponds to their isoelectric points. Because the gradient ampholytes and the samples stop where they have no mobility, the resistivity of the system increases dramatically toward the end of the experiment, and the current decreases dramatically. For this reason, isoelectric focusing is usually run with constant voltage. Constant current application can lead to overheating of the system.

The combination of sodium dodecyl sulfate (SDS), $CH_3(CH_2)_{10}CH_2OSO_3Na$, also known as lauryl sulfate, treatment of samples and polyacrylamide gel electrophoresis was first described in the late 1960s. SDS is an ionic surfactant which solubilizes and denatures proteins. The surfactant coats a protein through hydrophobic interactions with the polypeptide backbone, effectively separating most proteins into their polypeptide subunits. The majority of proteins to which SDS binds then unfold into linear molecules having a similar surface potential.

SDS-polyacrylamide gel electrophoresis (SDS-PAGE) allows separation of molecules strictly on the basis of size, i.e., molecular weight. When SDS-treated samples migrate into a gel and are electrophoresed, the principal difference is size or length. Smaller molecules travel through the matrix more quickly than those that are larger. The rate at which molecules migrate through a polyacrylamide gel is inversely linear with the logarithm of their molecular weight. Thus denatured samples can be analyzed alongside standards of known molecular weight to aid in the interpretation of a substance's physical size.

Two-dimensional (2D) electrophoresis is unique, offering an analytical method that is both reproducible and sensitive. It is referred to as 2D because it employs two different methods of electrophoresis, in two different dimensions, to produce one result. Each method separates the sample compounds based on different properties of each compound. The combination of the two methods gives better resolution of the compounds in the sample than could be achieved with either method alone. For example, each method alone may separate up to 100 components of a sample, whereas together they may separate up to 10,000 components.

A pair of electrophoretic techniques commonly employed in 2D analyses are the previously noted isoelectric focusing (IEF) and SDS-polyacrylamide gel electrophoresis (SDS-PAGE). IEF separates sample compounds according to isoelectric point, whereas SDS-PAGE separates the compounds by molecular weight. A 2D analytical technique using IEF and SDS-PAGE to separate proteins results in a gel having bands or spots in a random pattern. Each spot represents a unique component of a sample. A single charge difference in a component can be identified on the gel by a unique spot. This property of 2D electrophoresis, which allows identification of identical proteins that differ by one charge difference, has made it an invaluable technique for the molecular genetic community.

As noted, many proteins are separated by polyacrylamide gel electrophoresis (PAGE) (based on the molecular weight) or modified polyacrylamide gel isoelectric focusing (IEF) (based on molecular charge). Both of the techniques can be used in tandem in a two-dimensional approach for maximum resolution. Polyacrylamide gels are made by polymerizing the monomer, acrylamide, into long strands, and then linking the strands together with a cross-linker, usually N,N'-methylene-bis-acrylamide(bis). The relative proportions of these components will determine the separation characteristics of the gel. Isoelectric focusing is carried out in a PAGE gel that contains an immobilized pH gradient consisting of high molecular weight polyaminocarboxylic acid (ampholytes). The separation power of two dimensional polyacrylamide gel electrophoresis (2D PAGE) has often been exploited as part of isolation schemes for determining the amino acid sequence of unknown proteins from complex protein mixtures.

Particles can be manipulated by subjecting them to traveling electric fields. Such traveling fields are produced by applying appropriate voltages to microelectrode arrays of suitable design. Traveling electric fields are generated by applying voltages of suitable frequency and phases to the electrodes.

This technique of using traveling electric fields relates to an important method for separation and sorting of large particles and cells referred to as dielectrophoresis. Dielectrophoresis is defined as the movement of a polarisable particle in a non-uniform electric field. Essentially, the force arises from the interaction of the field non-uniformity with a field induced charge redistribution in the separated particle.

Particles are manipulated using non-uniform electric fields generated by various configurations of electrodes and electrode arrays. As a general biotechnological tool, dielectrophoresis is extremely powerful. From a measurement of the rate of movement of a particle the dielectric properties of the particle can be determined. More significantly, particles can be manipulated and positioned at will without physical contact, leading to new methods for separation technology.

A powerful extension of dielectrophoresis separation is traveling wave dielectrophoresis (TWD) in which variable electric fields are generated in a system of electrodes by applying time varying electric potential to consecutive electrodes. Such a method of Traveling Wave Field Migration was described by Parton et al. in U.S. Pat. No. 5,653,859, herein incorporated by reference. Although satisfactory, this work is not directed to the field of protein analyses and in particular, to gel electrophoresis techniques. In addition, dielectrophoresis requires higher voltages (~100 V), higher frequencies (~10 MHZ), and finer electrode pitch (<10 um)

A microfluidic device for electrophoretic separation of biomolecules such as DNA and protein was described by Dunphy et al. in "Rapid Separation and Manipulation of DNA by a Ratcheting Electrophoresis Microchip (REM)," Proceedings of IMECE2002, Nov. 17-22, 2002, New Orleans, La., No. IMECE2002-33564, herein incorporated by reference. The device utilizes thousands of electrodes along the length of a microchannel. An electrical potential is applied across the electrodes and selectively varied to separate molecules within the microchannel into two groups using a ratcheting mechanism. This mechanism does not employ traveling waves. Although directed to the separation of biomolecules, this strategy is based upon micro device technology and is not readily compatible with conventional laboratory proteomic equipment. Moreover, the strategy described by Dunphy et al. is silent with regard to applications involving gel electrophoretic techniques. Accordingly, a need exists for a device and technique for utilizing electrostatic traveling waves in conjunction with gel electrophoresis techniques and equipment.

Two-dimensional gel electrophoresis is the acknowledged workhorse for proteomic research because it is simple, has high capacity, and is able to identify all proteins resolved on the gel when coupled with a mass spectrometer. However, lengthy process time, difficulty in resolving low-abundance proteins, and poor reproducibility, among other factors, has limited its full potential to becoming the definitive tool for proteomics. The present subject matter addresses many of these issues with a new system design and technique to reduce processing time and increase analytical resolution by reducing band broadening with electrostatic traveling waves (TW).

BRIEF DESCRIPTION OF THE DISCOVERY

In a first aspect, a traveling wave grid assembly is provided which comprises a planar dielectric substrate and a plurality of electrically conductive and closely spaced electrodes disposed on the substrate. The electrodes extend parallel to one another and each define a first end and a second end opposite from the first end. The traveling wave grid assembly also comprises a layer of a gel material adapted for retention and migration of biomolecules dispersed therein. The traveling wave grid assembly also comprises a voltage controller adapted to provide an electrical signal having a plurality of phases. In addition, the traveling wave grid assembly comprises a plurality of electrically conductive buses that provide electrical communication between the voltage controller and the plurality of electrodes. The number of buses corresponds to the number of phases of the electrical signal provided by the controller. Each one of the buses is in electrical communication with both a first end and a second end of a corresponding electrode.

In another aspect, a traveling wave grid module adapted for use in a vertically integrated tiled system including at least another traveling wave grid module, is provided. The module comprises a planar dielectric substrate, a plurality of electrically conductive and closely spaced electrodes disposed on the substrate, a set of electrically conductive contact pads accessible along the substrate, and a plurality of electrically conductive buses. The electrically conductive electrodes extend parallel to one another and each defines a first and a second end. The plurality of electrically conductive buses provide electrical communication between the plurality of contact pads and the plurality of electrodes. Each one of the buses is in electrical communication with the respective electrode.

In another aspect, an electrophoretic cell is provided which has a plurality of traveling wave modules. The cell comprises a first planar substrate and a second planar substrate spaced from and generally parallel with the first substrate. The cell further comprises a plurality of traveling wave modules disposed between the first and second substrates. Each of the traveling wave modules includes a module base, a plurality of closely spaced electrodes extending across the base, a plurality of electrically conductive buses in electrical communication with the electrodes, a plurality of contact pads at which electrical communication to the buses is provided, and a layer of a suitable gel adapted for electrophoresis disposed adjacent the electrodes. The plurality of traveling wave modules are arranged between the first and second substrates so as to provide at least one column that includes at least two traveling wave modules. The modules in the column are in electrical communication with each other by electrical contact between respective contact pads of modules in the column.

In a further aspect, a system for separating, transporting or focusing biomolecules is provided. This system comprises a substrate and a plurality of closely spaced, parallel, electrically conductive electrodes disposed on the substrate. The system also comprises a layer of a material adapted for the retention and migration of biomolecules. The system also comprises a voltage controller in electrical communication with the plurality of electrodes. The voltage controller provides a four-phase electrical control signal to the plurality of electrodes. Depending upon the signal provided by the voltage controller, a particular model of transport is imparted to the biomolecules disposed in the layer.

Still further advantages of the present subject matter will become apparent to those of ordinary skill in the art upon reading and understanding the following detailed description of the preferred embodiments.

BRIEF DESCRIPTION OF THE DRAWINGS

The present subject matter may take form in various components and arrangements of components, and in various steps and arrangements of steps. The drawings are only for purposes of illustrating preferred embodiments and are not to be construed as limiting the present subject matter.

DETAILED DESCRIPTION OF THE PREFERRED EMBODIMENTS

Separation and identification of biomolecules such as proteins and DNA is an important step in biotechnology. In this post-genomic period, 2D gel electrophoresis is emerging as the workhorse for protein separation. The methodology is 30 years old and has seen mostly minor technology improvements. In one aspect of the present discovery, processing time is significantly reduced by a two step approach. First, an initial separation is performed using a distributed multi-segmented traveling wave (TW) electrode grid system which is optimized for enhanced protein loading and fast transport. Second, the sub-samples of separated proteins are further refined or focused by using specifically designed traveling wave processing algorithms on decoupled local traveling wave grids. The primary objective of using electrostatic traveling waves is the very rapid transport possible by creating very high local electric (E) fields with low voltages using an electrode grid with a very fine pitch. Advantages over conventional gel setups include lower voltage (1 V compared to 200 V for PAGE and 8 KV for IEF), and much higher transport velocities (up to 10 times or more).

In a first preferred embodiment, the present investigation provides a gel electrophoretic system comprising a thin layer of a gel medium disposed between two plates. One or more traveling wave grids extend along one or more interior faces of the plates and in contact with the gel. A first voltage source is provided and configured to apply a voltage potential across two opposite edges of the gel layer. Specifically, the first voltage source is in electrical communication with the traveling wave grid. As will be understood, the voltage potential causes biomolecules dispersed or applied to the gel, to travel from one edge or region toward the other edge or region of the gel layer. It is further preferred to provide a second voltage source and apply a voltage potential across the faces of the gel layer. The second voltage potential is preferably applied such that biomolecules in the gel layer are urged or "loaded" toward the traveling wave grid.

Figure 1A:
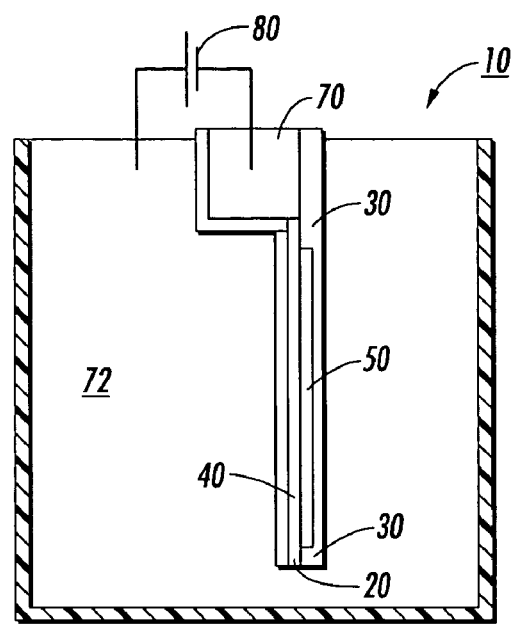
FIG. 1A is a schematic illustration of a preferred gel electrophoresis system.

FIG. 1A is a schematic illustration of a preferred embodiment gel electrophoresis system 10 comprising a thin layer 20 of a polyacrylamide gel cast between a glass plate 30 and a Plexiglas back plate 40. Gel thickness is controlled by appropriately placed Teflon shims. A traveling wave grid 50 is fabricated by depositing platinum electrodes on the glass 30. A thin layer of titanium may be used to improve adhesion of the platinum to the glass. The other plate may provide another identical traveling wave grid formed on glass to thereby provide a double-sided structure. The electrode and gel assembly is placed in electrical communication with a voltage source 80. One representative assembly is to immerse the electrode and gel assembly in a suitable electrically conductive buffer solution. Inner and outer chambers, designated as 70 and 72 respectively, contain the buffer solution. As will be appreciated, an electrical circuit is formed with the voltage source 80 such that the electrode and gel assembly provide the only path for the flow of electrons through the buffer solution to and from the voltage source 80. In addition, buffer solution in the outer chamber 72 also serves to cool the electrode and gel assembly immersed therein. The advantage of utilizing traveling wave grids on both sides of the gel is to either double the in-plane electric fields for the same gel thickness, or double the gel thickness for the same electric field. The latter may be especially useful if the protein packing capacity of the gel is important in order to attain a minimum level for sample detection. The ionic buffer such as the two buffer solutions in chambers 70 and 72 of FIG. 1A, serve as the two electrodes across which a DC field is applied. The protein sample is typically loaded onto the top of the gel and the electrophoretic current is forced to flow through the gel. In SDS-PAGE operation, the proteins or biomolecules in the sample migrate within the gel according to their molecular weight; with the lightest molecules migrating the furthest distance. In the schematic illustration of FIG. 1A, the migrating proteins flow downward through the layer 20 of gel.

Figure 1B:
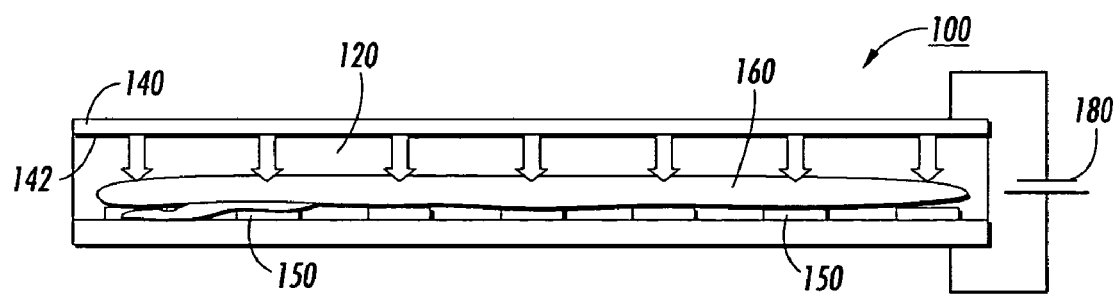
FIG. 1B is a schematic illustration of another preferred gel electrophoresis system.

Another preferred embodiment system as shown in FIG. 1B, utilizes a Plexiglas back plate 140 with a thin 200 Angstrom layer of platinum deposited on the inside face 142 of the plate 140 to contact the gel 120. A voltage source 180 is provided in electrical communication with the resulting electrode and gel assembly. The platinum forms a counter electrode which imparts electrostatic pressure to thereby load the proteins 160 against a traveling wave grid 150 so as to enhance protein loading as shown in FIG. 1B. For a 100 um thickness gel layer, only −0.1V is sufficient to provide the necessary electrostatic pressure for SDS treated negative proteins. This voltage is below the threshold of significant gas formation. It is contemplated that the embodiment of FIG. 1B for "loading" the proteins against the grid, may be used in conjunction with the embodiment of FIG. 1A, and other embodiments described herein.

Figure 2A:
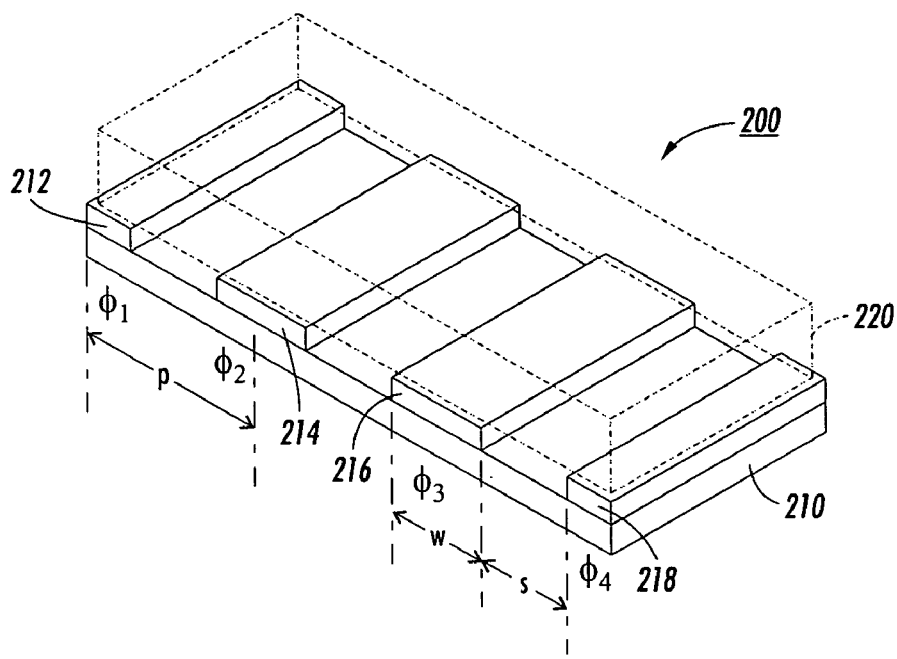
FIG. 2A is a schematic illustration of a preferred single sided traveling wave grid configuration with gel.
Figure 2B:
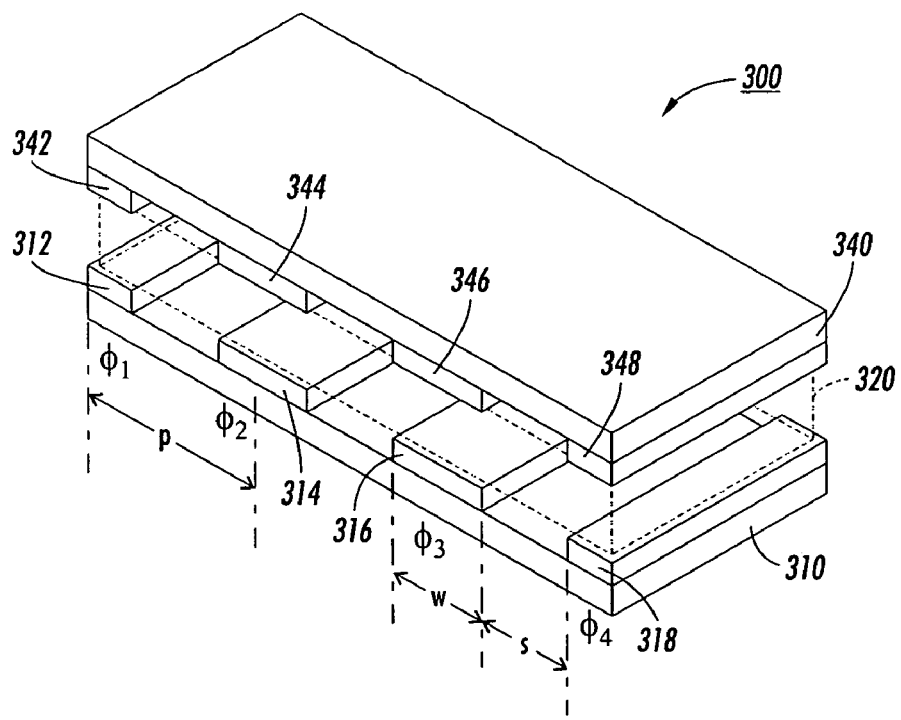
FIG. 2B is a schematic illustration of a preferred double sided traveling wave grid configuration with gel.

FIGS. 2A and 2B are schematic illustrations of preferred embodiment single and double sided traveling wave grid assemblies. The assemblies include an effective amount of a gel disposed in intimate relation thereto. Specifically, FIG. 2A is a single sided grid assembly 200 comprising a plate 210, a plurality of parallel and closely spaced electrodes 212, 214, 216, and 218, and an effective amount of a gel 220 in electrical communication with the electrodes. Most preferably, the electrodes are formed from platinum or alloys thereof. It is also preferred to deposit a thin layer of titanium on the plate, which is preferably glass, to promote adhesion between the electrodes and plate. As described herein, it is preferred to utilize a multi-phase, and most preferably, a four (4) phase electrical signal in conjunction with the preferred embodiment systems, assemblies, and grids noted herein. Accordingly, it is preferred that a first electrode such as electrode 212 be utilized for a first phase $\phi 1$, of the electrical signal. Similarly, it is preferred that a second electrode immediately adjacent to the first, such as electrode 214, be utilized for a second phase $\phi 2$ of the electrical signal. And, it is preferred that a third electrode immediately adjacent to the second electrode, such as electrode 216, be utilized for a third phase $\phi 3$ of the electrical signal. Moreover, it is preferred that a fourth electrode immediately adjacent to the third electrode, such as electrode 218, be utilized for a fourth phase $\phi 4$ of the electrical signal. As described in greater detail herein, the distance between the centers of adjacent electrodes is referred to as pitch, and denoted as "p." The width of an electrode is denoted as "w." And the distance between facing sidewalls or edges of adjacent electrodes is "s."

FIG. 2B is a schematic illustration of a preferred double sided traveling wave grid assembly 300 comprising a first plate 310; a first plurality of parallel and closely spaced electrodes 312, 314, 316, and 318; a second plate 340; a second plurality of parallel and closely spaced electrodes 342, 344, 346, and 348; and an effective amount of a gel 320 in electrical communication with the first and second plurality of electrodes.

Figure 3:
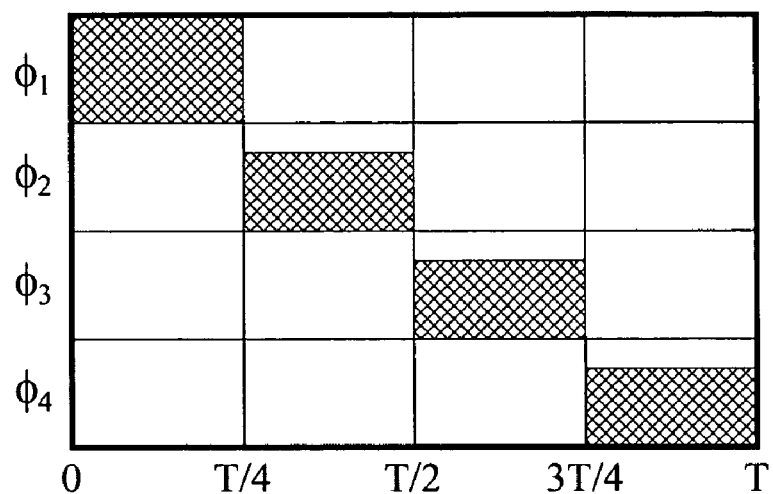
FIG. 3 is a representative four phase traveling wave voltage pattern employed in the preferred systems and traveling wave grids described herein.
Figure 4:
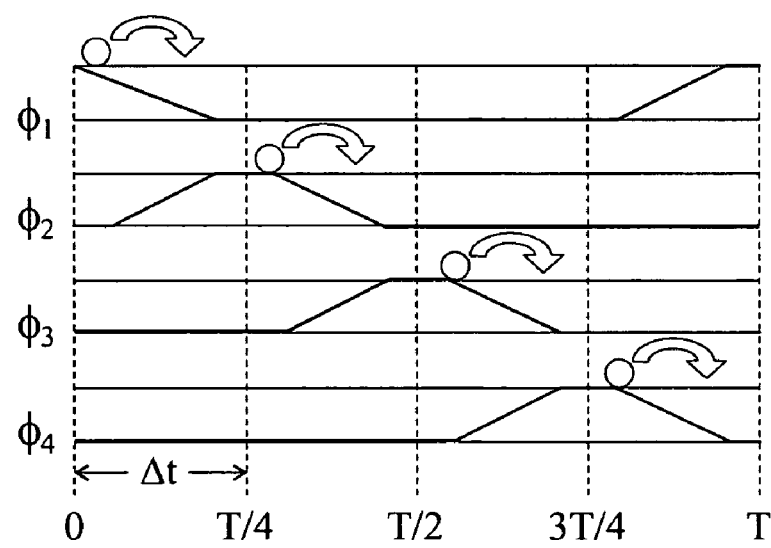
FIG. 4 is a schematic illustration of biomolecule transport from one electrode to another.

FIG. 3 is a representative four phase voltage pattern or waveform used in the preferred embodiment systems and traveling wave grids of the present invention. Specifically, FIG. 3 depicts the four phase voltage waveform with 90 degree separation between phases. Each waveform occurring in each phase is preferably a square wave pulse. Each pulse is sequentially applied to an adjacent electrode. Thus, a first pulse in phase $\phi 1$, is applied to a first electrode for a desired time period, such as T/4. Upon completion of that first pulse, such as at time T/4, a second pulse in phase $\phi 2$ is applied to a second electrode, preferably immediately adjacent to the first electrode. Upon completion of that second pulse, such as at time T/2, a third pulse in phase $\phi 3$ is applied to a third electrode, preferably immediately adjacent to the second electrode. Upon completion of that third pulse, such as at time 3T/4, a fourth pulse in phase $\phi 4$ is applied to a fourth electrode, preferably immediately adjacent to the third electrode. This sequential and ordered array of voltage pulsing results in biomolecules dispersed in the gel to "hop" from the vicinity of one electrode to another. The synchronous mode of propagation is depicted in FIG. 4 and may be described as a "hopping" mode where the biomolecules or proteins hop from electrode to electrode in the direction of the pulse train. The transit time to migrate across the dielectric space is then given by:

$$t_{transit} = s/\mu E,$$

where pitch is given by p=w+s, and w and s are the electrode width and dielectric space, respectively. Electric field and mobility are given by E and $\mu$, respectively. The period for one cycle through the 4-phases is $4*t_{transit}$, so that the maximum sweep frequency f is:

$$f < \mu E/4s.$$

For sustained transport, the protein has to have sufficient speed ($\mu E$) and time ($t_{transit}$) to traverse the distance of the dielectric space, s. This equation implies that for sustained transport, there is a critical frequency for proteins of a certain mobility. Therefore, by starting with the highest operational frequency, one can progressively scan downwards in frequency until the protein of the right mobility starts to move. This means that the fastest (and lowest molecular weight) proteins may be separated out from the sample of biomolecules one at a time.

In another preferred embodiment, the present discovery provides a gel electrophoretic system having a distributed multi-segmented traveling wave grid. The system includes a layer of a gel suitable for use in gel electrophoresis of biomolecules, a multi-segmented system of traveling wave grids, and a voltage controller in electrical communication with the grids. Each of the grid segments includes a plurality of closely spaced parallel electrodes that are in contact with the gel. The voltage controller is adapted to provide one or more selectable multi-phase electrical signals to one or more of the grid segments. In a particularly preferred embodiment, the voltage controller provides a first multi-phase electrical signal to at least one of the grid segments and a second multi-phase electrical signal to all or only some of the grid segments. In still other preferred aspects, the system may comprise two, three, or more voltage controllers that may be configured to provide one or more particular multi-phase electrical signals to one or more grid segments of the traveling wave grid.

Figure 5:
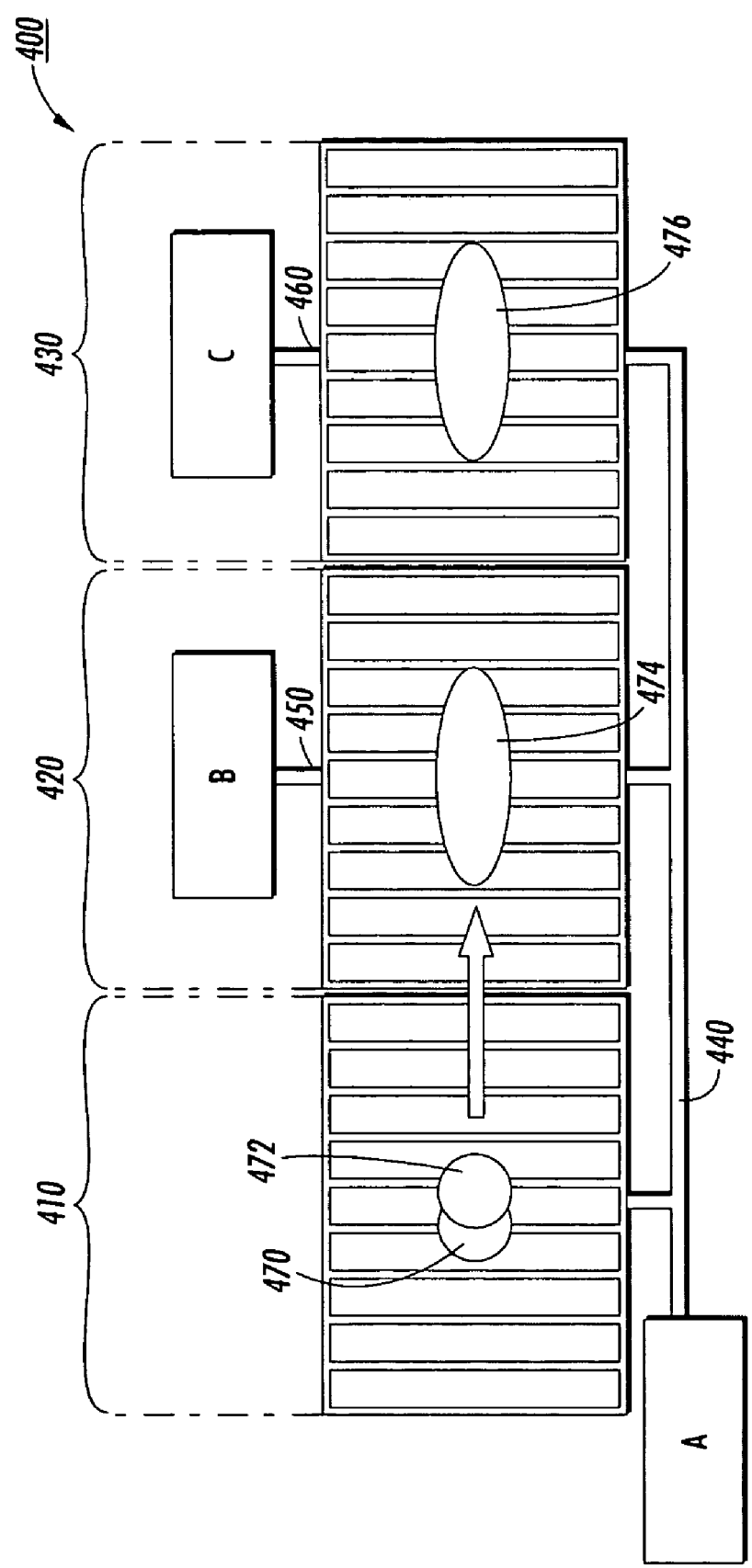
FIG. 5 is a schematic illustration of a preferred embodiment gel electrophoretic system utilizing distributed, reconfigurable, and reprogrammable traveling wave grids.

The present discovery provides significant opportunity for innovation in the design of specific waveforms to focus, separate, and concentrate proteins or other biomolecules and agents. One preferred strategy is to fabricate the smallest pitch possible for the traveling wave grids for maximum flexibility in reconfiguring them for specific applications. FIG. 5 is a schematic illustration of a preferred embodiment gel electrophoretic system 400 utilizing multiple distributed, reconfigurable, and reprogrammable traveling wave grids. Specifically, FIG. 5 illustrates a preferred multi-segmented traveling wave grid system. The preferred multi-segmented traveling wave grid system includes a first grid segment 410, a second grid segment 420, and a third grid segment 430. As will be appreciated, each segment includes a plurality of parallel and closely spaced electrodes. Two contiguous pads on respective sides together offer connection to the 4 phase circuit through one or more buses 440, 450, and 460. The system 400 preferably further includes one or more programmable voltage controllers such as controllers A, B, and C depicted in FIG. 5. As will be appreciated, the controllers are in electrical communication with the traveling wave grid (or segments thereof) through the noted buses.

In utilizing the preferred embodiment system 400, one particularly preferred strategy involves moving proteins of interest onto individual local traveling wave grid segments using controller A where they are then available for subsequent processing using controllers B, C and so forth. Each controller may be a separate PIC implementation or a single PIC with multiple pre-programmed instructions. For example, in operation, the preferred embodiment system 400 of FIG. 5 may be utilized to separate a sample of various biomolecules as follows. A sample 470 is deposited onto the grid segment 410. The sample migrates to region 472 and continues to migrate onto adjacent grid segment 420. Operation of system 400 continues until a region 474 of biomolecules forms within grid 420. Depending upon the biomolecules and grid parameters, the biomolecules constituting region 474 may further migrate to adjacent grid segment 430, and form a region 476 of biomolecules. Generally, this strategy utilizes an initial separation using a first controller and secondary refinements or further separation using other controllers and segments of grids. Secondary refinements include further concentrating of migrated biomolecules and focusing into bands or patches.

In still another preferred embodiment, the present discovery provides a process for separating various biomolecules from a sample. The process utilizes a gel electrophoretic system comprising a layer of a gel suitable for electrophoresis, the layer being disposed between two co-planar substrates. The system also includes a traveling wave grid which includes at least a first grid segment and a second grid segment. The system additionally includes a voltage controller in selective communication with the first grid segment and the second grid segment. The process comprises a first step of depositing the sample of biomolecules on the layer of the gel. Next, a first multi-phase electrical signal, such as a four phase electrical signal, is applied to one or both of the first and second grid segments. This causes at least a portion of the biomolecules in the sample to migrate in the gel. A second multi-phase electrical signal is applied to one or both of the first and second grid segments to further cause either the same portion of biomolecules to further migrate in the gel or another portion of biomolecules in the sample to migrate in the gel. By selectively applying appropriate multi-phase electrical signals to one or both of the grid segments, the sample can be selectively analyzed or separated.

If the system utilizes multiple voltage controllers, the process can further apply one or more multi-phase electrical signals generated by those additional controllers to various grid segments as desired. Additionally, each of the various voltage controllers used in this system may be configured to provide varying or changing multi-phase electrical signals. Changes in these signals may include changes in voltage levels, frequency, or other electrical parameters. Additionally, the present discovery includes processes in which the interface between a voltage controller and one or more of the traveling grids is changed. For instance, a multi-phase electrical signal may be applied to a particular array of electrodes in a grid. After a desired stage of the separation process has been reached, the electrodes to which the multi-phase electrical signal is applied are changed. This strategy may be used to selectively analyze and separate a wide array of biomolecules in a sample.

The present subject matter provides an electrophoretic cell that utilizes a collection of individual traveling wave modules. The modules may be arranged and configured such that a relatively large cell or grid is provided. For example, a traveling wave module is provided that includes a planar substrate such as glass, onto which are deposited a plurality of electrodes. As will be appreciated, preferably the electrodes are closely spaced, parallel to one another, and extend across the substrate. One or more contact pads are provided that provide electrical communication to the electrodes of the module. An effective amount of a suitable gel is deposited along the electrodes. The cell utilizes rows or columns of traveling wave modules that are arranged within the cell. Preferably, several columns are formed from a collection of modules. Each column may include two (2) or more modules. The modules within each column are preferably in electrical communication with each other by appropriate connection between their respective contact pads. Systems of these modules may be formed by forming multiple columns of modules between two spaced planar retaining substrates such as glass. Generally, each column contains 2 to 10 modules, and preferably from 3 to 6 modules. And a typical system may employ 2 to 20 columns and preferably 3 to 9 columns.

Figure 6A:
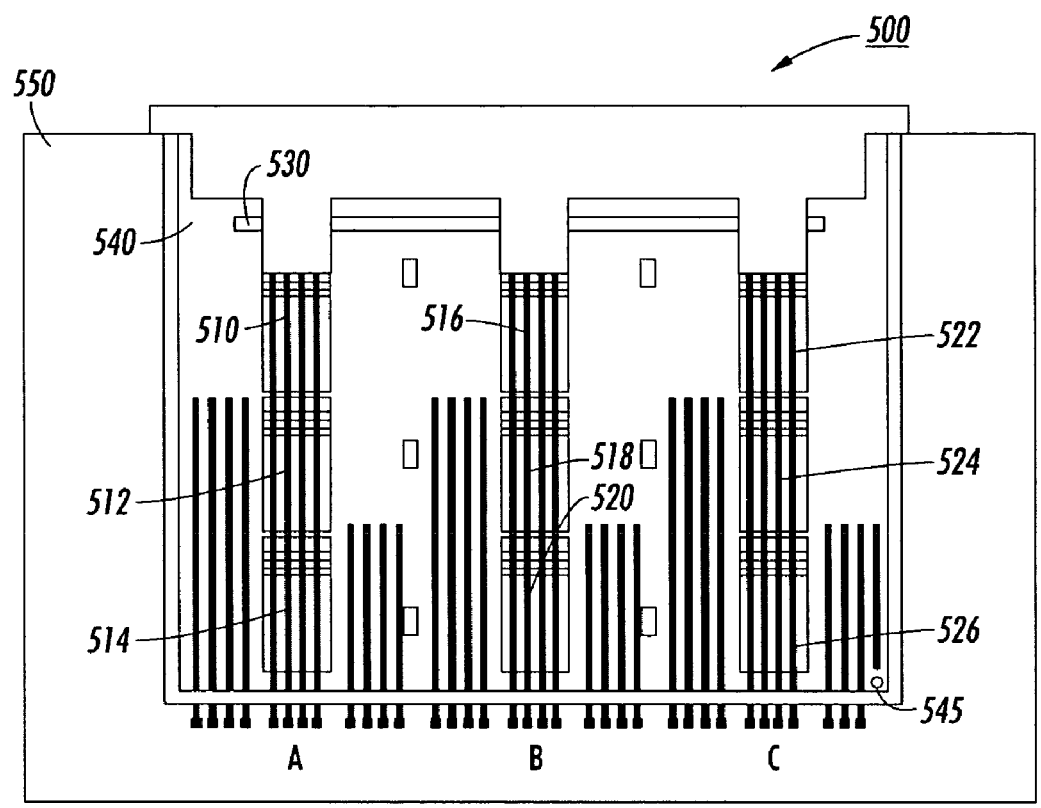
FIG. 6A is a schematic illustration of yet another preferred gel electrophoresis system.
Figure 6B:
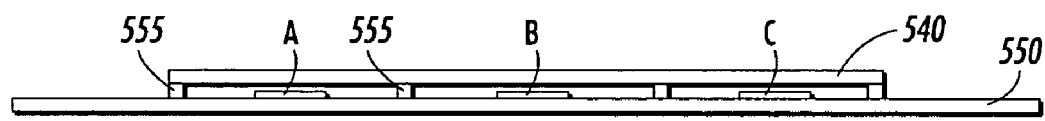
FIG. 6B is a cross-section of the preferred system depicted in FIG. 6A.
Figure 6C:
FIG. 6C is a detailed view of contact pads defined along a typical set of electrodes used in the preferred system shown in FIG. 6A.

A preferred gel cell 500 for protein separation is shown in FIGS. 6A, 6B and 6C. The system 500 comprises a pair of spaced plates 540 and 550, each preferably formed from glass. This preferred system includes a three-by-three (3×3) array of traveling wave modules, each 0.8 cm by 1.0 in dimension, with the traces no more than 0.8 cm in length, deposited onto a glass substrate. The 0.8 cm by 1.0 cm traveling wave modules are shown in FIG. 6A as 510, 512, 514, 516, 518, 520, 522, 524, and 526. These modules are arranged in three (3) columns shown in FIG. 6A as A, B, and C. Each column has a "well" into which a protein mixture can be loaded and used as a separate track for protein separation. FIG. 6A depicts this well as a protein loading electrode 530. Each column A, B, and C is a contiguous arrangement of three (3) modular traveling wave grids, all of which are powered in unison for the initial separation run. Thus, in the preferred embodiment depicted in FIG. 6A, column A includes modules 510, 512, and 514; column B includes modules 516, 518, and 520; and column C includes modules 522, 524, and 526. Secondary focusing and concentration can be performed on any or all of the three columns by addressing them separately with the appropriate traveling wave algorithms. The smaller glass counter plate 540 preferably has polymeric ridges along the two vertical sides and the bottom except for a bleed hole 545 defined at one corner. The ridges shown as 555 in FIG. 6B, are preferably formed from a polymer such as SU-8. SU-8 is also preferably used as the spacer to control gel thickness. Gel is loaded between the plates 540 and 550 via capillary forces by inverting the cell and dipping the upper opening into a wide beaker of gel. Electrical contact pads are external to the gel area. FIG. 6C is a detail view of a set of four contact pads 1-4.

In another aspect of the present discovery, the incorporation of traveling wave grids in large scale gel systems is addressed. Due to the low voltage (1V) and electrochemistry of such systems, voltage drop along traces becomes an issue. A low trace voltage would not sustain a high in-plane electric field. As will be appreciated, it is the relatively high in-plane electric fields resulting from traveling waves that results in rapid protein transport. Platinum is the electrode material of choice as it is most resistant to electrophoresis and corrosion. However, it is also 6.5 times less conductive than copper. To consider the combination of issues relating to gel resistance, trace resistance, and so forth, several designs were analyzed to identify a configuration which provides characteristics that are uniform with trace length.

Figure 7:
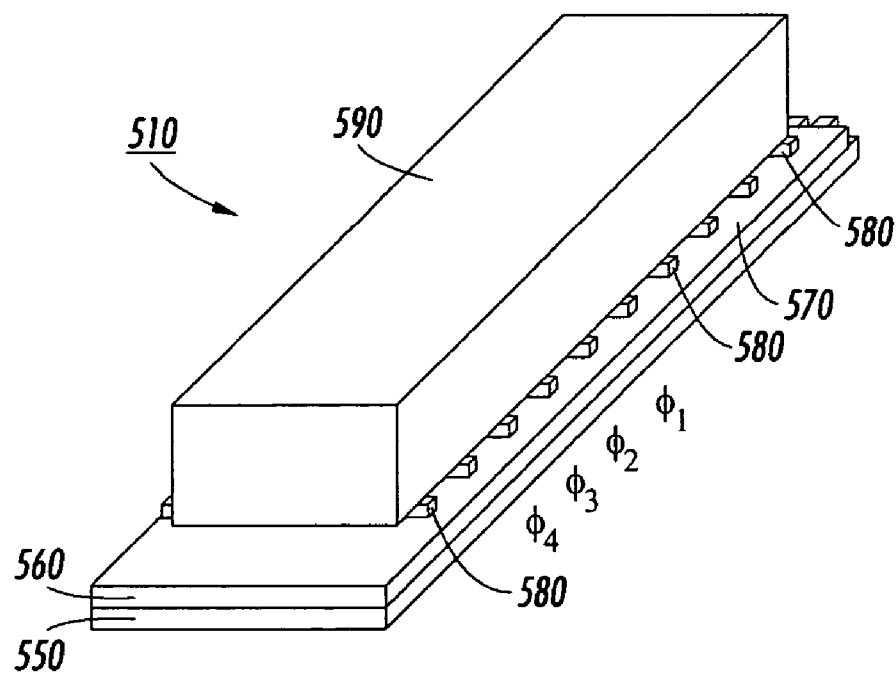
FIG. 7 is a perspective view of a preferred traveling wave module used in the system shown in FIGS. 6A-6C with a counter plate removed to illustrate the interior configuration of the module.

FIG. 7 is a perspective view of a preferred vertically integrated traveling wave module used in the system of FIGS. 6A-6C shown without the counter plate 540. Platinum electrodes are fabricated on an insulator like oxynitride or BCB, with vias connecting them to large cross-section bus lines beneath the insulator. Specifically, although the module shown in FIG. 7 is denoted as module 510, it will be appreciated that any and all of the modules 510-526 shown in FIG. 6A preferably utilize a similar configuration. The module 510 of FIG. 7 comprises a glass substrate 550 on which is disposed a layer 560 of an electrically conductive material that serves as a bus or as a ground plane, as described herein. Preferably, layer 560 is formed from copper or aluminum. A layer 570 of an electrical insulator is disposed on the conductive layer 560. As noted, a preferred insulator is oxynitride or BCB. A plurality of traveling wave electrodes 580 are disposed on the electrical insulator 570. As will be appreciated, an effective amount of a suitable gel 590 is disposed on and about the electrodes 580. Defined along an end region of the gel 590 are one or more vias. This integrated structure minimizes the surface area or "footprint" of the traveling wave module.

Figure 8:
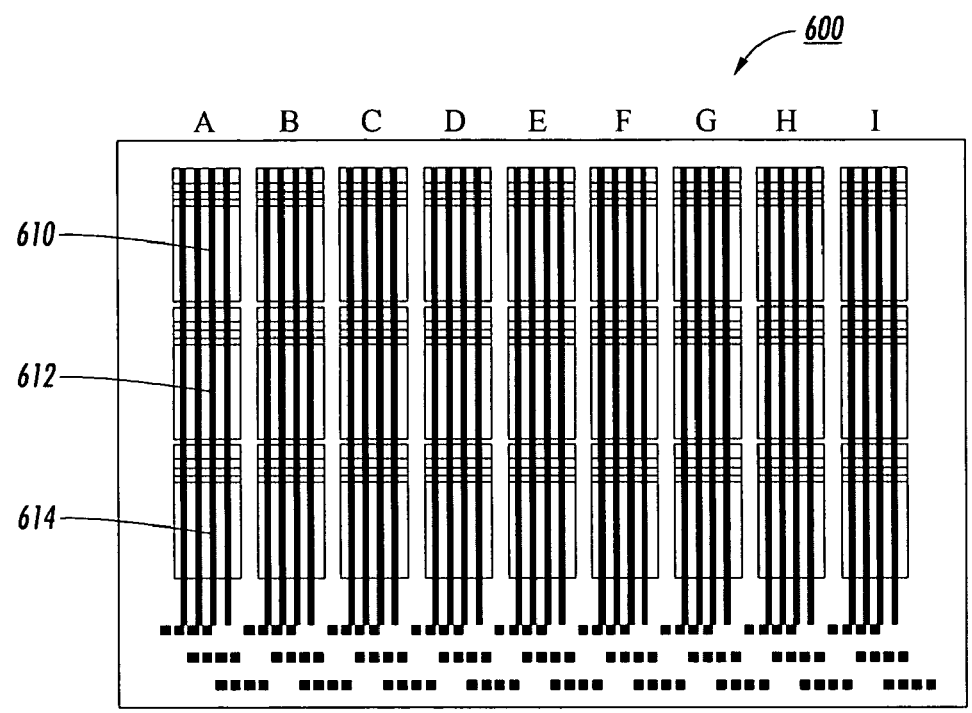
FIG. 8 is a schematic illustration of another preferred gel electrophoresis system.

For scalable use, arrays of the traveling wave modules can be tiled as shown in FIG. 8 to suit a desired cell or gel size. An advantage of this strategy is that voltage drops are limited to the trace dimension. Specifically, FIG. 8 is a schematic illustration of another preferred gel electrophoresis system 600. System 600 includes a three-by-nine (3×9) array of traveling wave modules. That is, the system 600 includes nine (9) columns A-I, each column containing three (3) modules. For example, column A includes modules 610, 612, and 614. Each of the modules used in system 600 has a configuration like that of the previously described module 510 depicted in FIG. 7.

Figure 9:
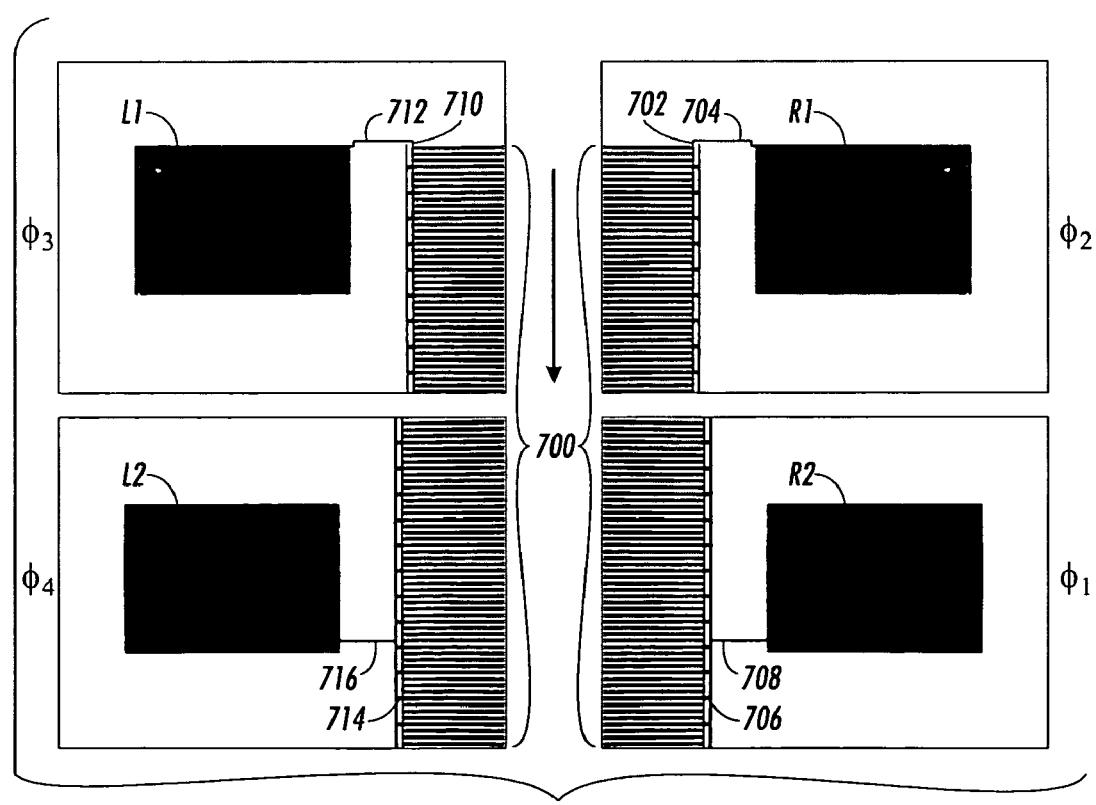
FIG. 9 is a schematic illustration of a plurality of contact pads used to provide access to a traveling wave grid.

FIG. 9 illustrates a typical electrode layout for any of the preferred systems described herein. Specifically, FIG. 9 illustrates four (4) contact pads that are used to access or provide electrical communication to buses that in turn, are in electrical communication with the traveling wave electrodes. For instance, contact pad R1, which may be designated for phase $\phi 2$ of the multi-phase voltage waveform applied to a traveling wave grid 700, is in communication with bus 702 by conductive trace 704. Similarly, contact pad R2, designated for phase $\phi 1$ applied to grid 700, is in communication with bus 706 by conductive trace 708. Contact pad L1, designated for phase $\phi 3$ applied to grid 700, is in communication with bus 710 by conductive trace 712. And, contact pad L2, designated for phase $\phi 4$ applied to grid 700, is in communication with bus 714 by conductive trace 716. The arrow in FIG. 9 illustrates the direction of electrostatic traveling waves induced across the grid 700.

In a preferred embodiment, a traveling wave grid assembly is provided in which a collection of parallel electrodes are selectively energized or powered by one or more voltage controllers that supply a multi-phase electrical signal to the collection of electrodes. One or more buses are used that provide electrical communication between the electrodes and the controllers. In one preferred configuration, one or more of the buses provide electrical signals to only one end of the electrodes. In another preferred configuration, the buses provide electrical signals to both ends of the electrodes. Details of these two configurations are described in greater detail herein.

Figure 10A:
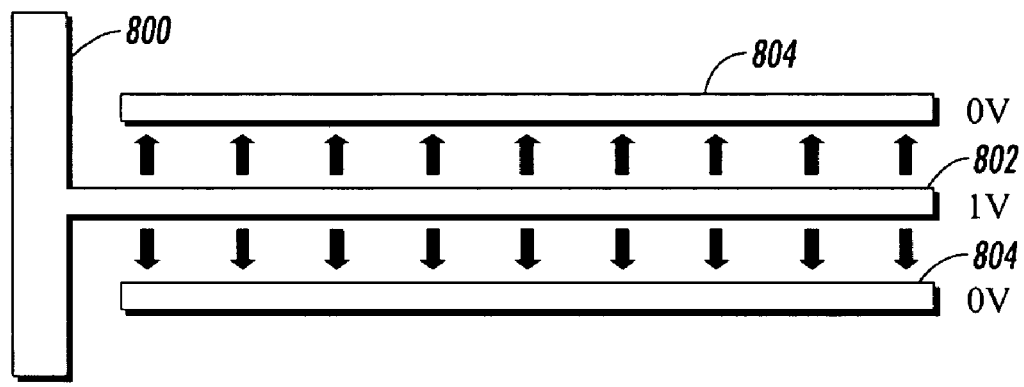
FIG. 10A is a schematic view of a single bus and traveling wave grid configuration.
Figure 10B:
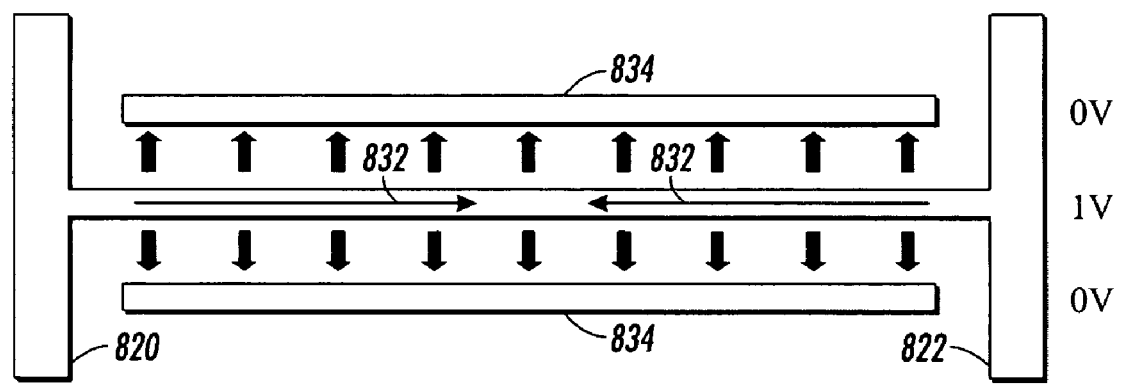
FIG. 10B is a schematic view of a dual bus and traveling wave grid configuration.
Figure 11A:
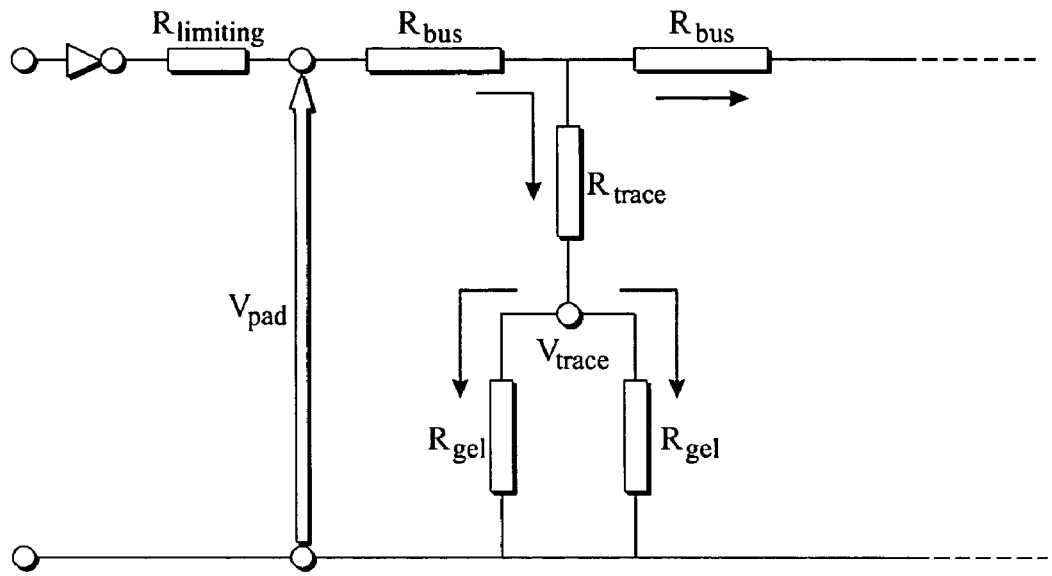
FIG. 11A is a schematic of an equivalent circuit for the single bus configuration depicted in FIG. 10A.
Figure 11B:
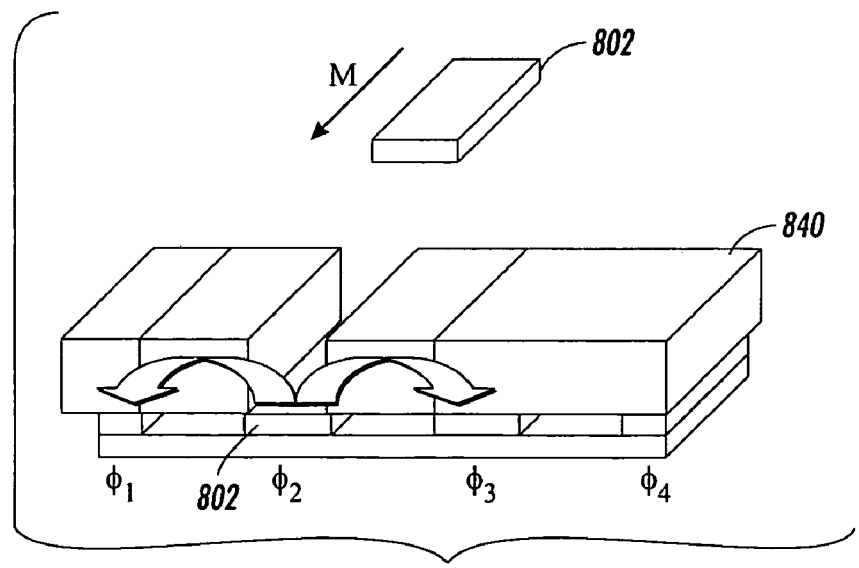
FIG. 11B is a perspective schematic view of an electrode powered from one end, and the incorporation of that electrode in a traveling wave grid.
Figure 12A:
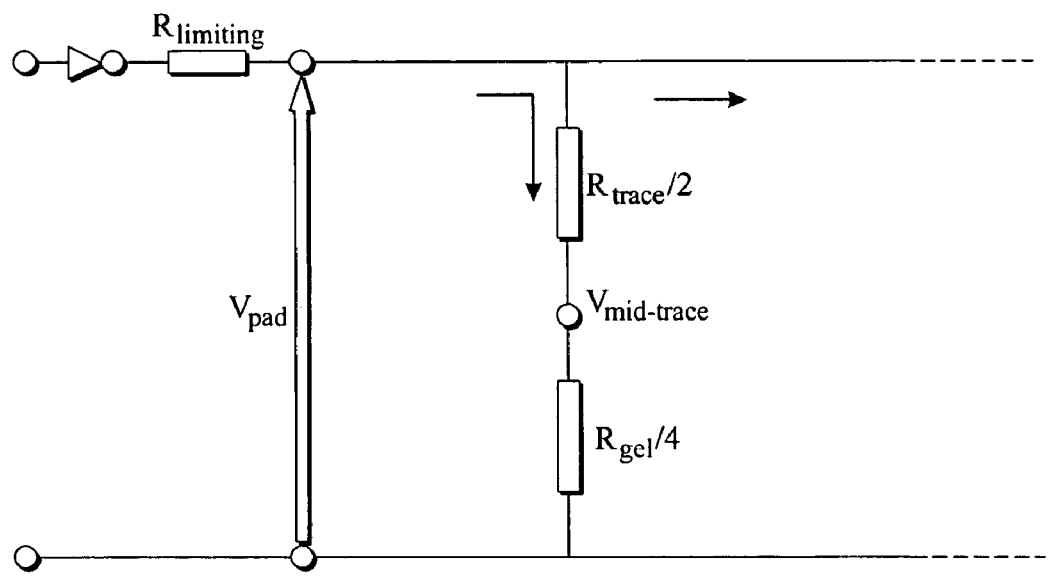
FIG. 12A is a schematic of an equivalent circuit for the dual bus configuration depicted in FIG. 10B.
Figure 12B:
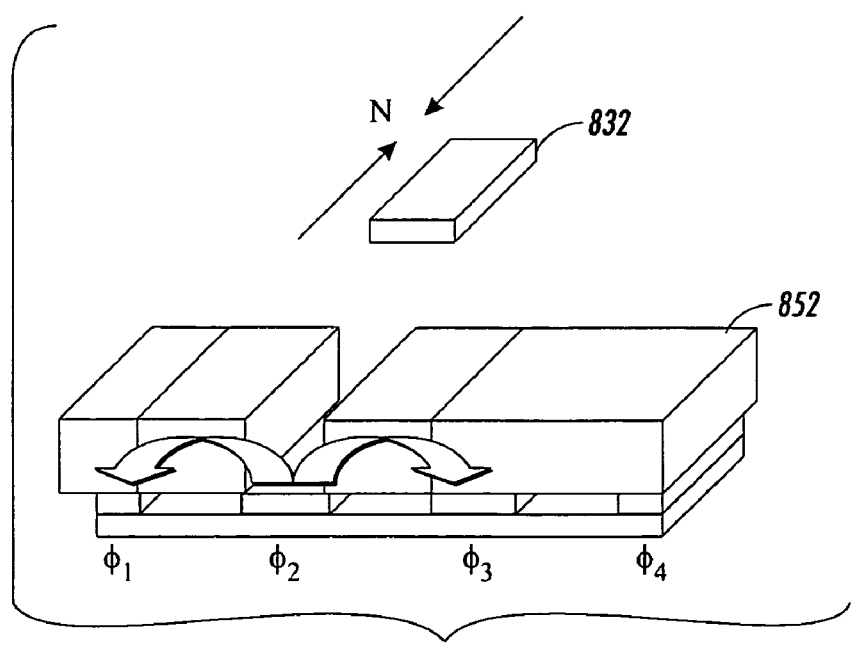
FIG. 12B is a perspective view of an electrode powered from both ends, and the incorporation of that electrode in a traveling wave grid.

FIGS. 10A and 10B show circuit considerations for driving a 4-φ assembly. FIG. 10A is a single bus line design applicable for traveling wave grids where the voltage drops along the entire length of the trace. Current flows from a single bus line 800 into an energized center electrode 802 and then through gel to two neighboring electrodes or a ground 804. FIG. 10B is a double bus line version which features a voltage drop only along half the trace length. In FIG. 10B, current flows from two buses 820 and 822 into an energized center electrode 832 and then through gel to two neighboring electrodes or a ground 834. The equivalent circuit for the single bus line is shown in FIG. 11A. The equivalent circuit for the double bus line is shown in FIG. 12A. FIG. 11B is a perspective schematic view of the electrode 802 of FIG. 10A and its incorporation in a traveling wave grid and gel assembly 840. The direction of current flow through the electrode 802 is designated by arrow M. FIG. 12B is a perspective view of the electrode 832 depicted in FIG. 10B and its incorporation in a traveling wave grid and gel assembly 852. The direction of current flow through the electrode 832 is designated by arrow N.

In the preferred embodiment in which each bus is in electrical communication with one or both ends of a respective electrode, a representative four phase configuration may be as follows. A first electrode of a traveling wave grid is in electrical communication with a first bus. Either one or both of its ends are in electrical contact with an electrical bus that in turn provides communication with an output phase of a voltage controller. A second electrode of the grid, preferably adjacent to the first electrode, is in communication with a second bus. Either one or both ends of the second electrode are in electrical contact with a second bus that provides communication with another output phase of the controller. This configuration is preferably followed for each phase of the controller. Thus, if the controller provides a four (4) phase signal, this configuration is used for each set of four electrodes of the grid.

Neglecting the short bus distance between 4-φ groups which are preferably 160 um apart in many of the preferred systems, the equivalent trace and gel resistance are used to compute current and voltage parameters as set forth in Table 1.

TABLE 1

Parameters for Single and Double Bus Line Traveling Wave Grids

| | System 1 | | | | System 2 | | | |
|---|---|---|---|---|---|---|---|---|
| | Single bus | | Double bus | | Single bus | | Double bus | |
| | | | | Metal | | | | |
| Parameter | Cu | Pt | Cu | Pt | Cu | Pt | Cu | Pt |
| $\rho_{gel}$ Ω-cm | 324 | 324 | 324 | 324 | 324 | 324 | 324 | 325 |
| $\rho_{trace}$ Ω-cm | $17e^{-7}$ | $110e^{-7}$ | $17e^{-7}$ | $110e^{-7}$ | $17e^{-7}$ | $110e^{-7}$ | $17e^{-7}$ | $110e^{-7}$ |
| $W_{trace}$ um | 19 | 19 | 19 | 19 | 10 | 10 | 10 | 10 |
| $h_{trace}$ um | 0.15 | 0.15 | 0.15 | 0.15 | 0.15 | 0.15 | 0.15 | 0.15 |
| pitch um | 30.5 | 30.5 | 30.5 | 30.5 | 40 | 40 | 40 | 40 |
| spacer um | 11.5 | 11.5 | 11.5 | 11.5 | 30 | 30 | 30 | 30 |
| dc % | 62.3 | 62.3 | 62.3 | 62.33 | 25.0 | 25.0 | 25.0 | 25.0 |
| $W_{gel}$ cm | 0.8 | 0.8 | 0.8 | 0.8 | 0.8 | 0.8 | 5.0 | 5.0 |
| $L_{gel}$ cm | 1.0 | 1.0 | 1.0 | 1.0 | 1.0 | 1.0 | 4.0 | 4.0 |
| $h_{gel}$ um | 100.0 | 100.0 | 100.0 | 100.0 | 100.0 | 100.0 | 100.0 | 100.0 |
| Eff $h_{gel}$ um | 7.705 | 7.705 | 7.705 | 7.705 | 20.10 | 20.10 | 20.10 | 20.10 |
| $V_{pad}$ V | 1.0 | 1.0 | 1.0 | 1.0 | 1.0 | 1.0 | 1.0 | 1.0 |
| $R_{gel}$ Ω | 604.5 | 604.5 | 1208.9 | 1208.9 | 1208.9 | 1208.9 | 193.4 | 193.4 |
| $R_{trace}$ Ω | 47.72 | 308.8 | 23.86 | 154.4 | 45.33 | 293.3 | 283.3 | 1833.3 |
| $R_{phase}$ Ω | 350.0 | 611.0 | 314.2 | 379.4 | 324.9 | 448.7 | 190.0 | 965.0 |
| $n_{group}$ | 81 | 81 | 81 | 81 | 62 | 62 | 250 | 250 |
| $R_{equiv}$ Ω | 4.32 | 7.54 | 3.88 | 4.68 | 5.24 | 7.24 | 0.76 | 3.86 |
| $I_{total}$ mA | 231.5 | 132.6 | 257.8 | 213.5 | 190.8 | 138.1 | 1315.6 | 259.1 |
| $I_{phase}$ mA | 2.86 | 1.64 | 3.18 | 2.64 | 3.08 | 2.23 | 5.26 | 1.04 |
| Δ $V_{trace}$ mV | 136.4 | 505.3 | 37.97 | 203.4 | 69.76 | 326.7 | 745.5 | 949.9 |
| *$V_{trace}$ V | 0.864 | 0.495 | 0.962 | 0.797 | 0.930 | 0.673 | 0.254 | 0.050 |
| $P_{phase}$ mW | 2.468 | 0.810 | 3.060 | 2.100 | 2.860 | 1.500 | 1.340 | 0.052 |
| $P_{total}$ mW | 199.9 | 65.57 | 248.0 | 170.0 | 177.5 | 92.99 | 334.8 | 12.98 |

In Table 1, "$\rho_{gel}$" and "$\rho_{trace}$" are the resistivity of the gel and trace (or electrode), respectively. "$W_{trace}$" is the width of the trace. "$h_{trace}$" is the height of the trace. "Pitch" is the distance between centers of adjacent traces. "Spacer" is the dielectric spacer between adjacent traces. The designation "dc" is the duty cycle. "$W_{gel}$" is the width of the gel. "$L_{gel}$" is the length of the gel. The notation "$h_{gel}$" is the height of the gel. "Eff $h_{gel}$" is the effective height of the gel after E field compression. "$V_{pad}$" is the voltage as measured at the contact pad. "$R_{gel}$" is the resistance of the gel. "$R_{trace}$" is the resistance of the trace. "$R_{phase}$" is the resistance of the phase. The designation "$n_{group}$" is the number of four phase groups. "$R_{equiv}$" is the equivalent resistance of the grid. "$I_{total}$" is the current flow through the grid. "$I_{phase}$" is the current flow through an individual phase of a four phase group. "$\Delta V_{trace}$" is the voltage drop across a trace. "$*V_{trace}$" is the average voltage of a trace. "$P_{phase}$" is the power consumption of a phase. "$P_{total}$" is the power consumption of the grid.

Figure 13:
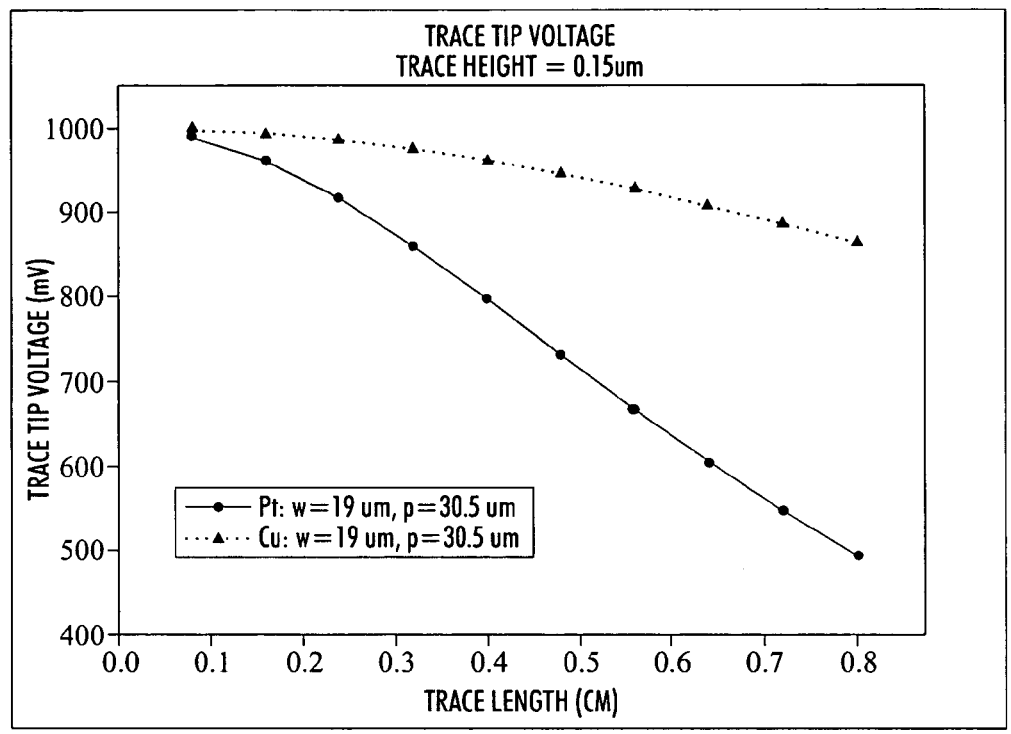
FIG. 13 is a graph illustrating trace voltage drop as trace length is varied for a single bus line configuration.
Figure 14:
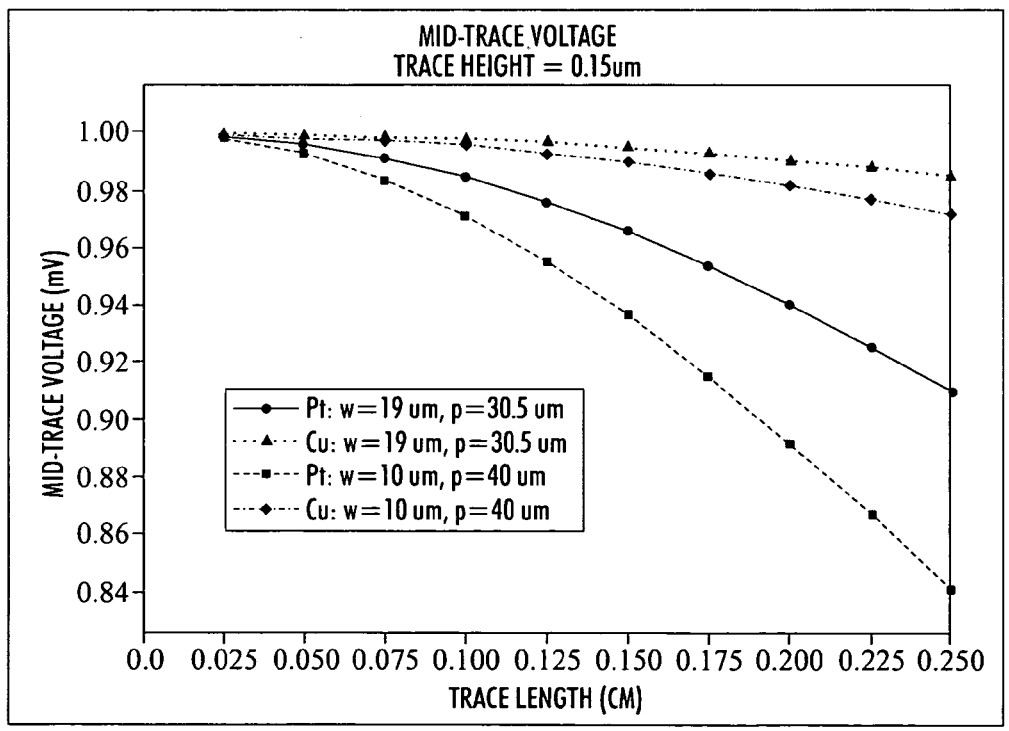
FIG. 14 is a graph illustrating trace voltage drop as trace length is varied for a dual bus line configuration.

Referring to Table 1, it is clear that the double bus line configuration results in a voltage drop of 0.2V over 0.8 cm trace length with platinum compared to 0.5V for the single bus line configuration. These results are for a traveling wave grid having 30.5 um pitch and 63% duty cycle. For more optimal operation, the preferred embodiment is 40 um pitch and 25% electrode duty cycle. The corresponding voltage drop for a platinum trace is 0.326V as shown in column 7 of Table 1. This can be compensated by increasing the pad voltage from 1V to 1.5V so that the voltage level remains below the threshold of significant gas formation. Trace voltage drops for both the single bus and double bus line configurations are shown in FIGS. 13 and 14, respectively.

Figure 15A:
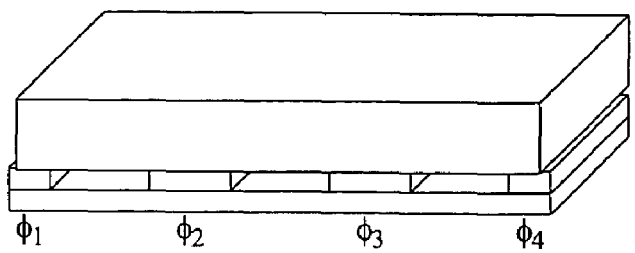
FIG. 15A is a perspective schematic view of a single sided traveling wave grid.
Figure 15B:
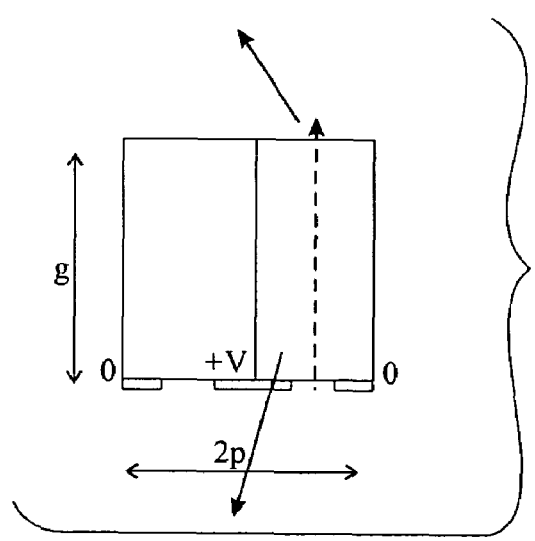
FIG. 15B is a diagram of an analysis used to optimize gel thickness.
Figure 15C:
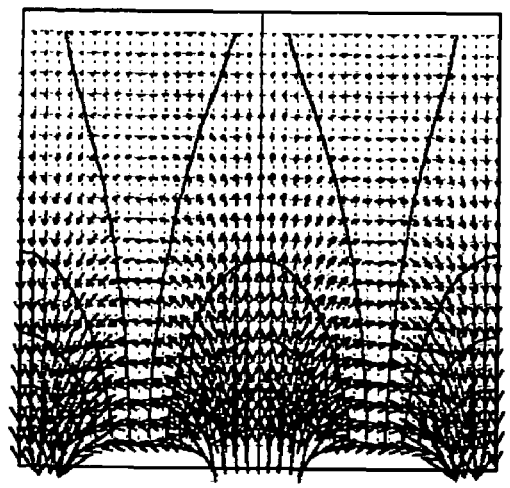
FIG. 15C is an illustration of a resulting electric field extending about two electrodes in a traveling wave grid.

In another aspect of the present discovery, the dual bus lines are disposed below the upper traveling wave grids and separated by a thin insulator material such as oxynitride or BCB. Each of the preferred eight (8) bus lines may be up to 1 mm in width and use a large cross-section to minimize voltage drop. Since the thickness of the insulator may present fabrication problems, an analysis may be performed to determine the thinnest layer that can be used and which will not impact the in-plane electric fields in the gel. FIGS. 15A, 15B, and 15C are presented for purposes of performing such an analysis.

To determine the preferred thickness of the gel, such as in the assembly of FIG. 15A, two electric field averages are computed to determine sensitivity. A cross-section average is computed through the thickness of the gel in the mid-spacer region of the traveling wave grid. This gel thickness is illustrated as g in FIG. 15B. The mid-spacer plane extending through the gel is shown as the dashed line. The cross-section E field average may be calculated by:

$E_x$ Surface Norm=$\int E_x \, dy / \int dy$

A volume average is also computed in the symmetry region between the mid-point of the electrode and the mid-point of the spacer. This volume E field average may be calculated by:

$E_x$ Volume Norm=$\int \int E_x \, dxdy / \int \int dxdy$

As will be appreciated by those skilled in the art, the gel thickness may be optimized by selecting parameters that lead to relatively large values of $E_x$ Surface Norm and $E_x$ Volume Norm. Higher electric fields such as depicted in FIG. 15C lead to greater amounts of mass or particle movement along the traveling wave grid.

Figure 16A:
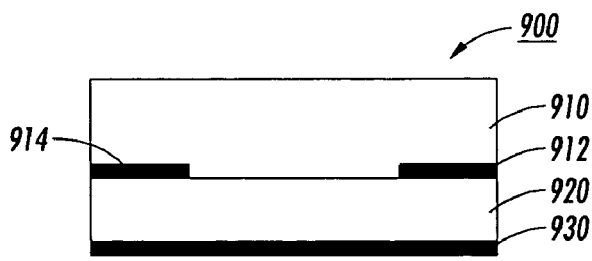
FIG. 16A is a schematic view of a preferred assembly of electrodes and gel, utilizing a ground plane.
Figure 16B:
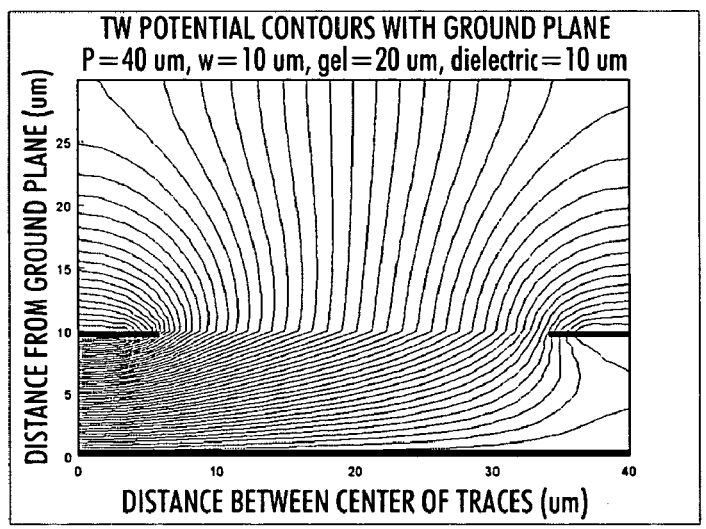
FIG. 16B is a plot of the electric field extending between adjacent electrodes in the assembly of FIG. 16A.
Figure 16C:
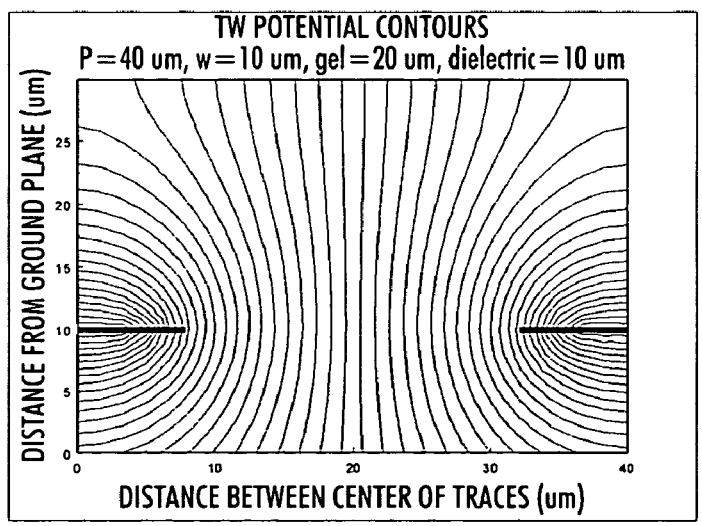
FIG. 16C is a plot of the electric field extending between the noted electrodes of FIG. 16A, however without the presence of a ground plane.

FIGS. 16B and 16C show electric potential contours for two embodiments; one in proximity with a ground plane and the other with the ground plane farther away or, essentially removed. Specifically, FIG. 16A is a schematic view of an assembly 900 comprising two adjacent electrodes 912 and 914 disposed between an upper layer of gel 910 and a lower layer of a dielectric 920. An optional electrically conductive layer 930 is disposed on the other side of the dielectric. The layer 930 may be in the form of a bus providing access to an electrical signal. FIGS. 16B and 16C illustrate the effect of the layer 930 upon the electric fields extending about the electrodes 912 and 914. FIG. 16B illustrates the electric field with the presence of the layer 930. FIG. 16C illustrates the electric field without the presence of the layer 930. FIGS. 16B and 16C demonstrate the effect of a ground plane upon the resulting electric fields between and extending about electrodes of a traveling wave grid.

Figure 17:
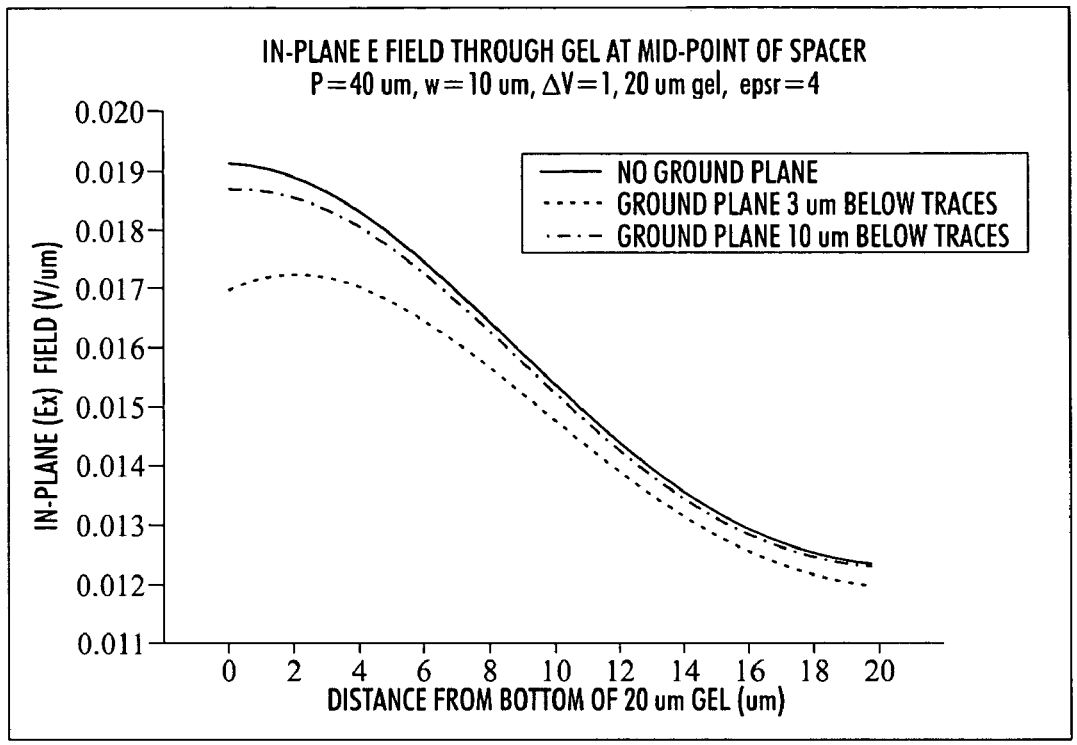
FIG. 17 is graph of the in-plane electric field through a layer of gel.

The in-plane electric field distribution through the gel, plotted along the mid-point of the spacer, is shown in FIG. 17. The three curves correspond to thicknesses of 3 um, 10 um and infinity (a case where the bus lines would not be under the traveling wave grids). Although the curve for 10 um thickness appears to be attractive, it would be a challenge to fabricate. A 3 um thickness is selected as the design parameter.

Figure 18:
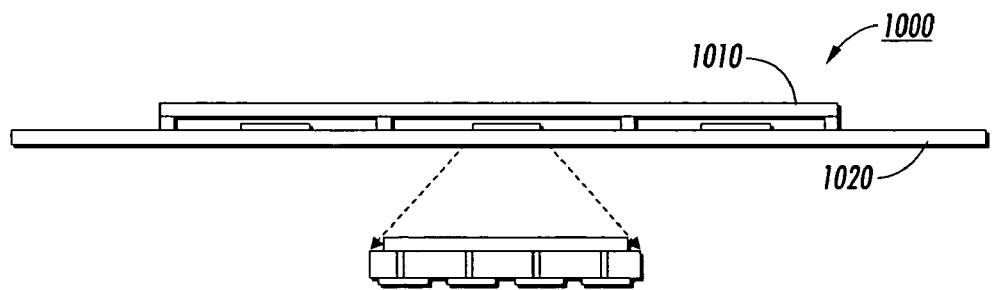
FIG. 18 is a schematic view of another preferred assembly.

FIG. 18 is a schematic view of a cross section of another preferred assembly 1000 in accordance with the present discovery. FIG. 18 resembles the cross section of FIG. 6B. Assembly 1000 comprises a plurality of traveling wave grids or columns of traveling wave modules disposed between a pair of spaced plates 1010 and 1020. Average electric field values are tabulated in Table 2 for the system represented in FIG. 18. Generally, as will be appreciated, the larger the value of the electric field, the better the performance of the resulting traveling wave grid.

TABLE 2

Average Electric Field Values for
Several Dielectric Thicknesses and Constants

| Dielectric Thickness <um> | Dielectric Constant | $E_x$ (x-sec. ave) <mV/um> | $E_x$ (vol. ave) <mV/um> |
| --- | --- | --- | --- |
| 3 | 4 | 14.753 | 12.696 |
| 10 | 4 | 15.428 | 13.009 |
| ∞ | 4 | 15.590 | 13.051 |
| 3 | 5 | 14.473 | 12.784 |
| 10 | 5 | 15.317 | 12.963 |
| ∞ | 5 | 15.523 | 13.020 |

In another aspect of the present discovery, it is preferred to incorporate a plurality of electrically conductive buses into a stacked or laminate assembly and to utilize vias to provide electrical communication between the buses and desired electrodes. For example, in a preferred embodiment, a layer of an electrical insulator is provided between a traveling wave grid and a plurality of buses. The buses may be oriented such that they extend in a plane parallel with the traveling wave grid and its associated electrodes. Although parallel, the buses preferably extend at right angles to the electrodes in certain embodiments. The one or more electrically conductive vias are provided in the stacked assembly which provide electrical contact between a bus and one or more electrodes. Preferably, the vias extend through the layer of electrical insulation and provide electrical communication between a bus and select locations on an electrode. Vias are preferably formed by a variety of techniques, but may include depositing a copper-based material into an aperture formed in the layer of electrically insulating material.

Figure 19:
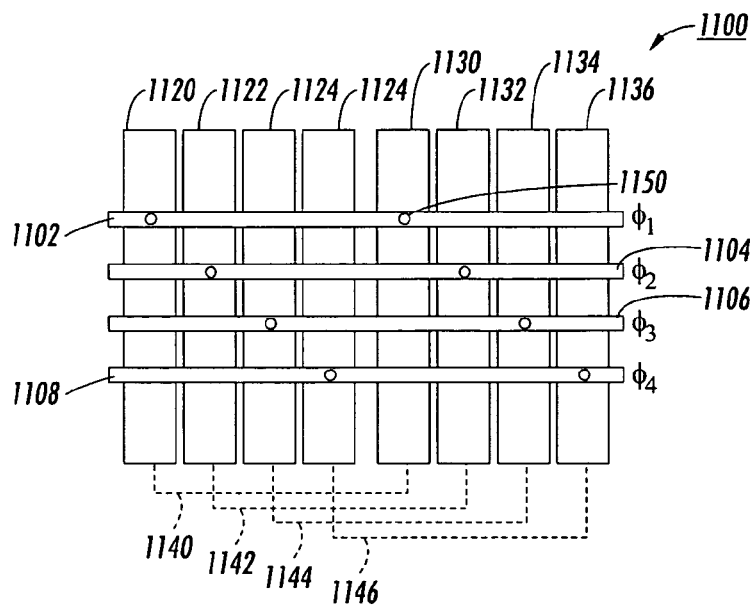
FIG. 19 is a schematic view of yet another preferred assembly.

A preferred system is shown in FIG. 19 where in addition to copper vias to connect the platinum traces to the sub-layer bus lines, terminal connections of relatively large cross section are also used at one end of the system to further minimize voltage drops. The spacing between vias is such that the voltage drop is limited to less than half a trace length. Specifically, FIG. 19 illustrates a preferred configuration and orientation of bus lines and electrodes. The system 1100 shown in FIG. 19 comprises a plurality of traveling wave electrodes 1102, 1104, 1106, and 1108. In addition, the system 1100 comprises a plurality of buses 1120, 1122, 1124, 1126, 1130, 1132, 1134, and 1136. Individual buses may be placed in electrical communication with other buses by one or more traces, such as traces 1140, 1142, 1144, and 1146. Electrical communication between an individual bus and a respective electrode is preferably provided by a via. For example, in the system 1100 shown in FIG. 19, via 1150 provides electrical communication between bus 1130 and electrode 1102.

A wide array of materials may be used in fabricating the electrodes, buses, and vias described herein. Generally, any electrically conductive material may be used although metals or alloys are preferred. For the electrodes, platinum is preferred to withstand the electrochemistry. The vias preferably include copper. And, the buses are preferably formed from copper or aluminum.

Figure 20A:
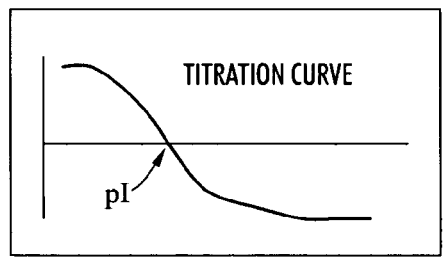
FIG. 20A is a representative titration curve for a protein and its isoelectric point.
Figure 20B:
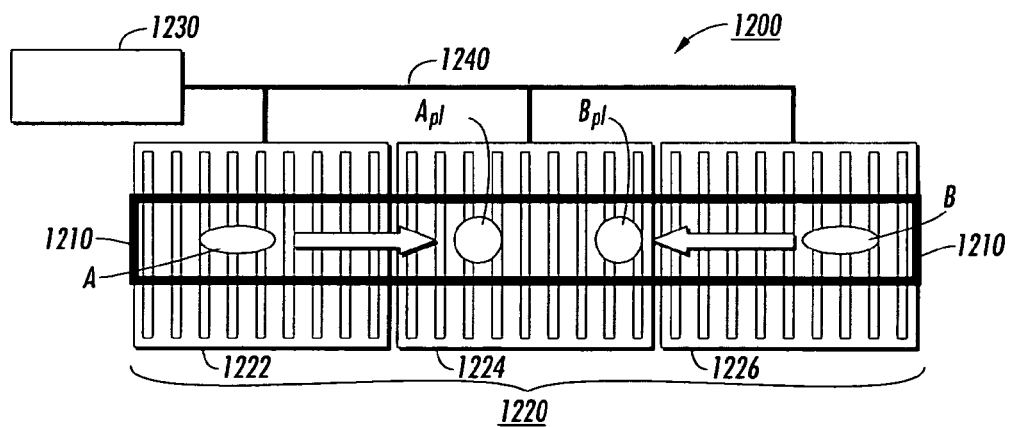
FIG. 20B is a schematic illustration of a preferred multi-segmented traveling wave grid and immobilized pH gradient strip system.

In another aspect of this subject matter, a traveling wave signal is used to simultaneously move both positively and negatively charged biomolecules or agents, and preferably proteins, to their isoelectric point, i.e. pI. FIG. 20B shows a top view of a preferred embodiment system 1200 comprising an immobilized pH gradient (IPG) strip 1210 disposed on a multi-segmented traveling wave grid 1220. The grid 1220 preferably includes a first traveling wave grid module 1222, a second traveling wave grid module 1224, and a third traveling wave grid module 1226. Each of the modules are in electrical communication with a traveling wave voltage controller 1230 through one or more buses 1240. The charge behavior of a typical protein as a function of pH gradient is shown in the representative titration curve of FIG. 20A. A 4-φ positive electrode voltage pattern is provided by the controller 1230 to transport the proteins toward their isoelectric point where they stagnate. As shown in FIG. 20B, a first protein is deposited onto the IPG at location A. Upon operation of the system 1200, that protein may migrate to a new location designated as $A_{pI}$. That new location may correspond to the isoelectric point of the first protein. The system 1200 is configured such that a second protein for example, may be applied onto the IPG at location B and concurrently with the transport of the first protein, may be transported in an opposite direction to new location $B_{pI}$.

Figure 21A:
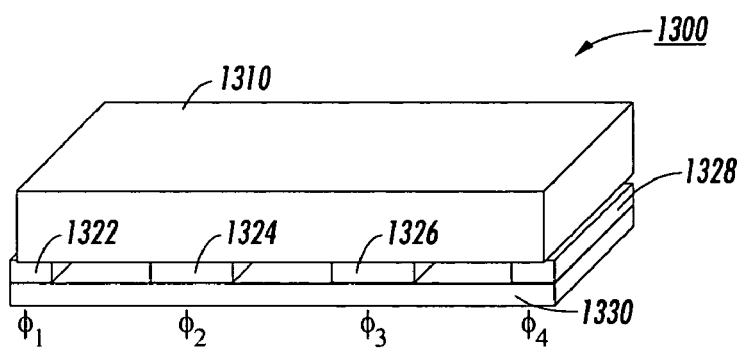
FIG. 21A is a schematic illustration of a portion of the traveling wave grid used in the system of FIG. 20B.
Figure 21B:
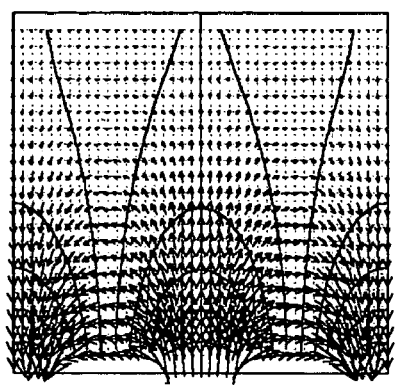
FIG. 21B is an illustration of the electric field resulting from traveling waves imparted to the electrodes shown in FIG. 21A.

FIG. 21A illustrates a single-sided embodiment of a portion of the traveling wave grid used in the previously described system 1200. FIG. 21B illustrates the corresponding fringing electric field vectors between a center electrode and two adjacent neighboring electrodes. Specifically, FIG. 21A illustrates an assembly 1300 including a plurality of electrodes 1322, 1324, 1326, and 1328 disposed between a layer of gel 1310 and a substrate 1330. The resulting electric field extending about the electrodes is shown in FIG. 21B. Another embodiment may utilize double-sided traveling wave grids, in which case, the electric field advantage would be doubled for the same gel thickness or the gel thickness can be doubled.

A significant feature of the present work is the design of a specific voltage pattern to selectively move both positively and negatively charged proteins in opposing directions at the same time. Before describing this feature, it is instructive to consider traveling waves and their effect upon molecules or charged species. Generally, there are two modes of propagation using traveling waves. The synchronous mode of transport is the fastest and is directly related to the phase velocity of the traveling wave signal. In this mode, proteins are relatively close to the grid surface and 'hop" from electrode to electrode in response to the sweep frequency. The asynchronous mode of transport describes the proteins which are further away from the grid surface and which never contact the electrode surfaces. Instead, they move in a "curtain" fashion at velocities which are a fraction of the synchronous speed. The divisor is the number of phases used.

Figure 22:
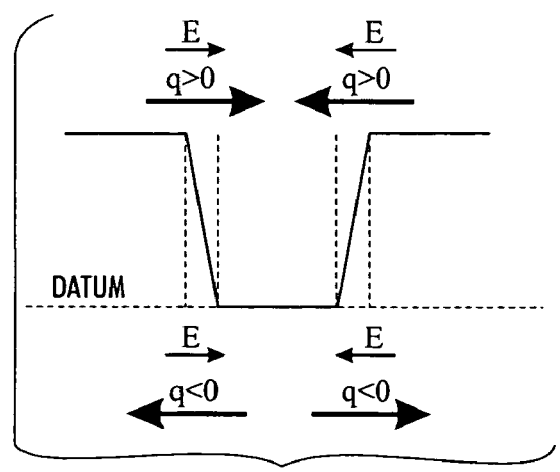
FIG. 22 is a schematic diagram illustrating aspects of biomolecule transport.

The mechanics of transport are shown in FIG. 22 where the interval between two sequential voltage pulses may be used for illustration. The four combinations of electric field (designated as E) direction and charge polarity (designated as q) dictates the preferred direction of motion in each case. On the trailing edge of the voltage pulse, the electric field is in the direction of the wave sweep. Therefore, positively charged proteins move forward (to the right with reference to FIG. 22). Negatively charged proteins exhibit a tendency to move backwards or toward the left in FIG. 22. On the leading edge of the voltage pulse, the electric field is in the opposite direction to the wave sweep. Therefore, positively charged proteins now exhibit a tendency to move backwards or to the left in FIG. 22. Negatively charged proteins will now move in the direction of the wave sweep, or forward or to the right as shown in FIG. 22. The dominant transport combinations are for positively charged proteins on the trailing edge and negatively charged proteins on the leading edge. Between the voltage pulses, the compacting effect on positively charged proteins and small diverging effect on negatively charged proteins account for some asymmetry in their respective transport rates.

Figure 23A:
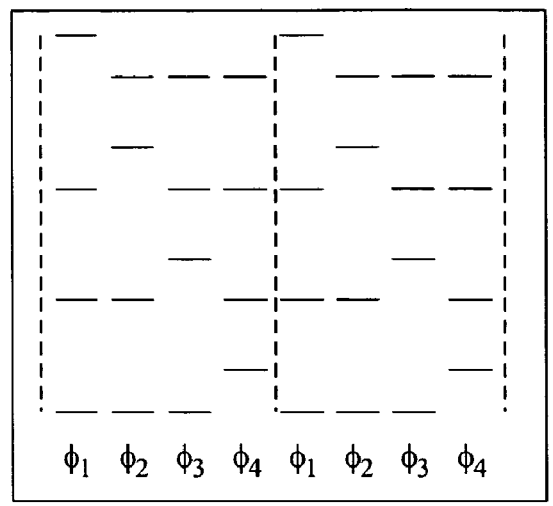
FIG. 23A is a schematic diagram illustrating a spatial voltage distribution on two contiguous four phase electrode groups, for a preferred algorithm.
Figure 23B:
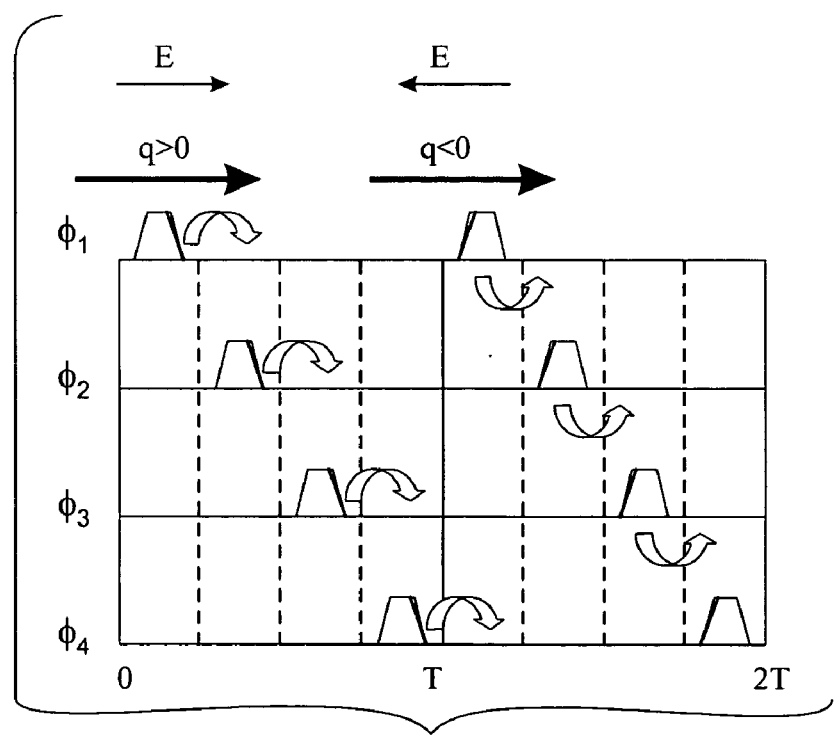
FIG. 23B is a schematic diagram illustrating a temporal voltage distribution for each of the four phases depicted in FIG. 23A and uni-directional protein transport.

FIGS. 23A and 23B illustrate an algorithm for unidirectional forward transport of both positively and negatively charged proteins. FIG. 23A represents the spatial voltage distribution on two contiguous 4-φ electrode groups. The temporal voltage distributions for each of the four phases are shown in FIG. 23B. This algorithm exploits the trailing edge for positively charged protein motion and the leading edge for negatively charged protein motion. Both species move in the direction of the voltage sweep.

Figure 24:
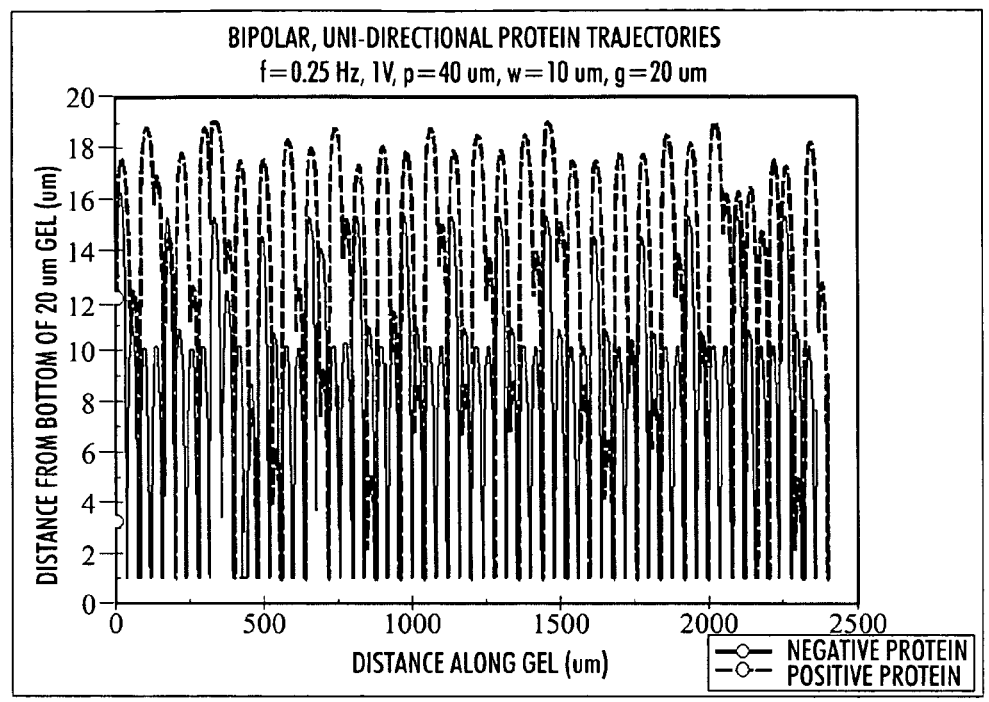
FIG. 24 is a graph of trajectories of a positively charged protein and a negatively charged protein on a traveling wave grid in which the proteins are undergoing uni-directional transport.
Figure 25:
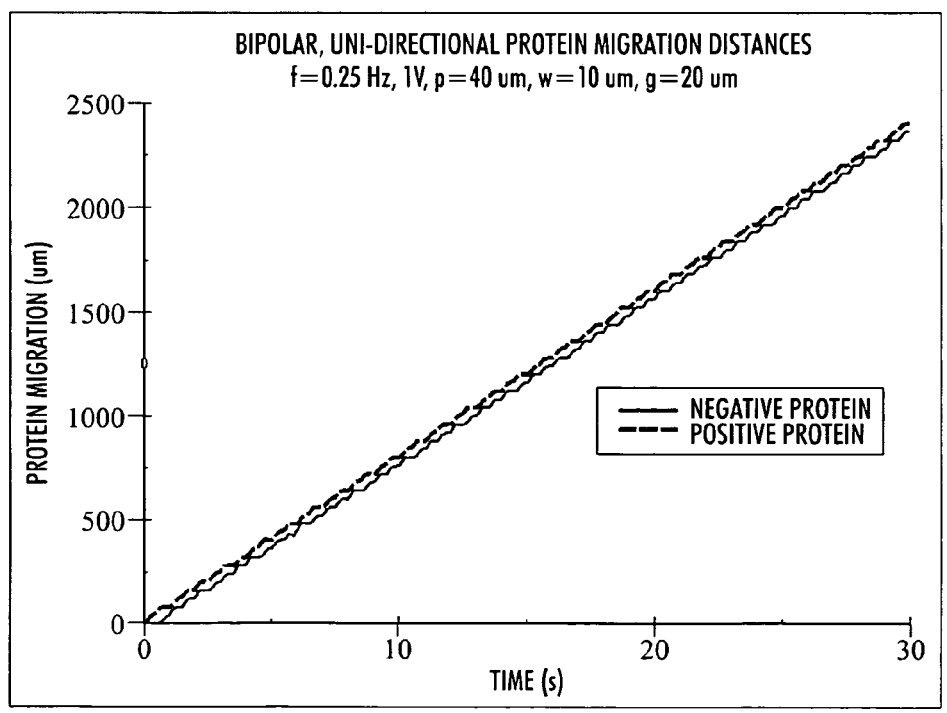
FIG. 25 is a graph of migration distances of the proteins undergoing uni-directional motion and plotted in FIG. 24.

Sample "hopping" trajectories of a positively charged protein and a negatively charged protein are shown in FIG. 24. Simulation parameters are typical for 20 um thickness gel, 1V traveling wave pulses, 4-φ signal, 50 um pitch at 25% electrode duty cycle and a protein molecular weight of 13.7 kDa for Ribonuclease A. Because of the positive voltage used in the traveling waves, the positively charged protein undergoes larger excursions away from the grid. However, because there is a considerable period of residency on each electrode, this difference in path length does not introduce a delay which leads to spreading. Migration distances in the lateral direction are shown in FIG. 25. The separation between the two curves represents the temporal spacing between the voltage pulses. This separation is maintained. The gradient is the propagation velocity and is identical for both charge species.

Figure 26A:
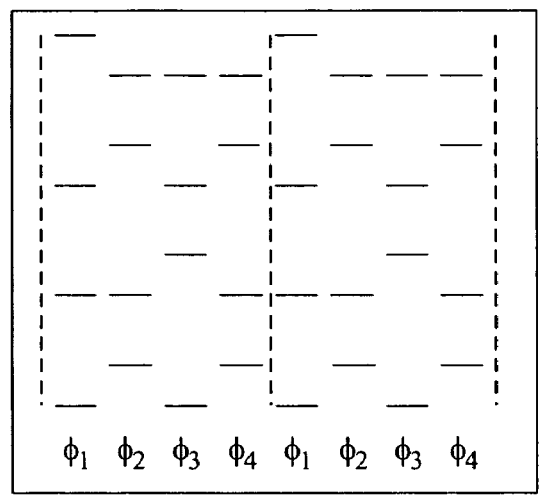
FIG. 26A is a schematic diagram illustrating a spatial voltage distribution on two contiguous four phase electrode groups, for another preferred algorithm.
Figure 26B:
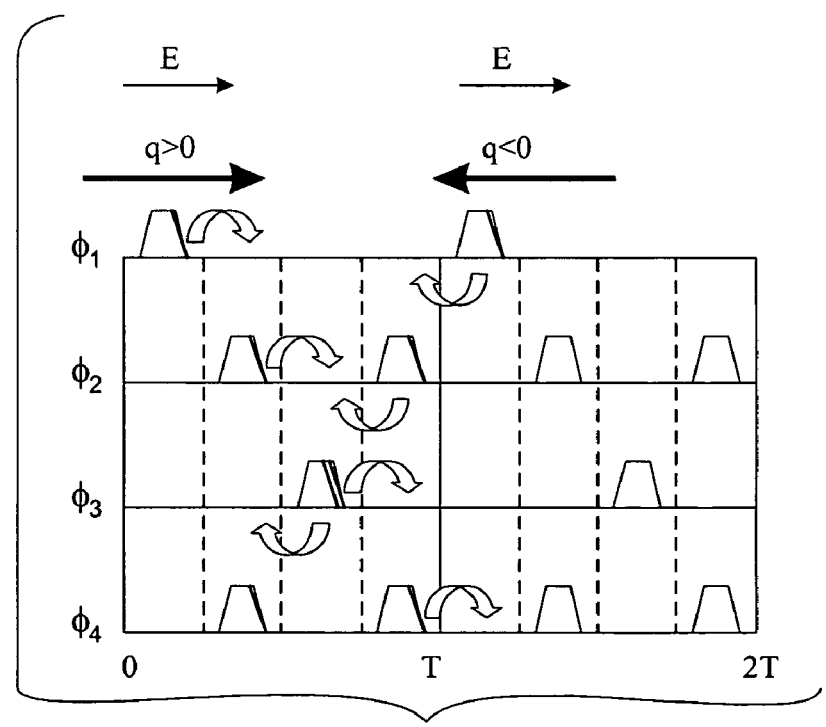
FIG. 26B is a schematic diagram illustrating a temporal voltage distribution for each of the four phases depicted in FIG. 26A and bi-directional protein transport.

FIGS. 26A and 26B illustrate another algorithm for bi-directional transport of both positively and negatively charged proteins. The spatial voltage distribution on two contiguous 4-φ electrode groups is shown in FIG. 26A. The temporal voltage distributions for each of the four phases are shown in FIG. 26B. The strategy is to exploit the trailing edge to allow positively charged protein motion in the direction of wave travel (to the right as shown in FIG. 26B). The negatively charged protein also uses the trailing edge so that it moves opposite to the direction of wave travel (to the left in FIG. 26B). This is achieved by inserting a voltage pulse on a succeeding electrode prior to the new pulse on the present electrode which acts to divert the flow of the negative proteins.

Figure 27:
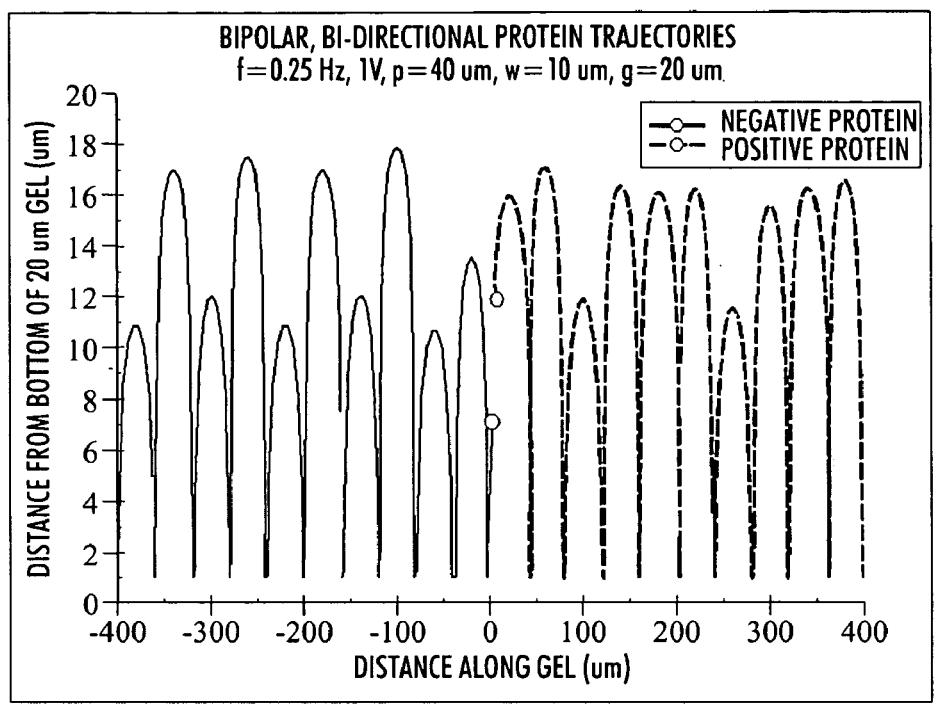
FIG. 27 is a graph of trajectories of a positively charged protein and a negatively charged protein undergoing bi-directional transport as shown in FIG. 26B.
Figure 28:
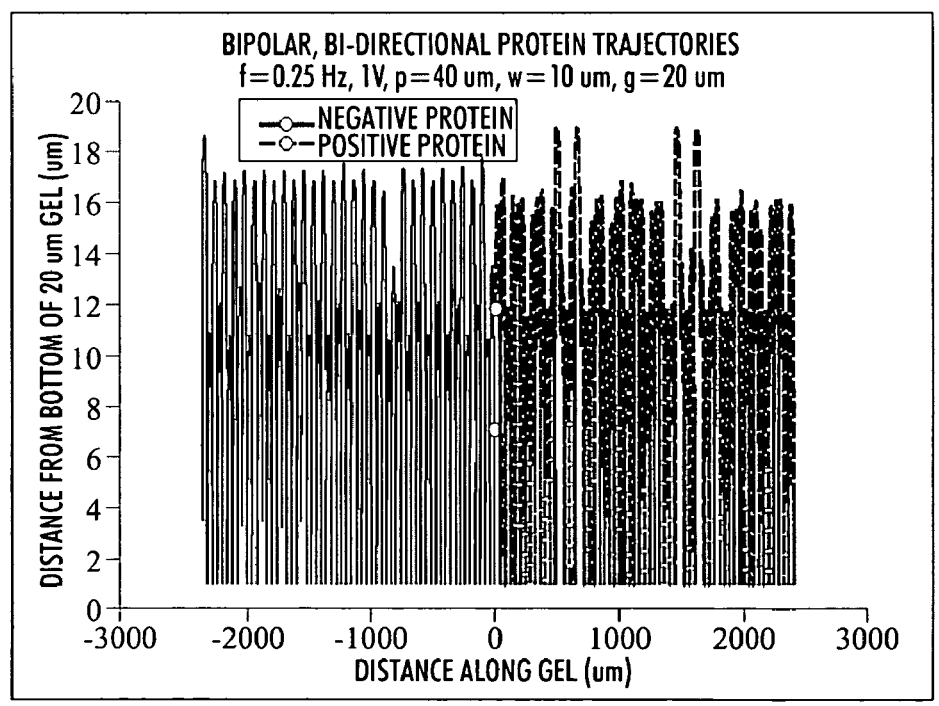
FIG. 28 is another graph of trajectories of the positively charged and negatively charged proteins of FIG. 26B.

FIGS. 27 and 28 illustrate sample trajectories moving in opposing directions for the two charge species discussed in conjunction with FIGS. 26A and 26B.

Figure 29:
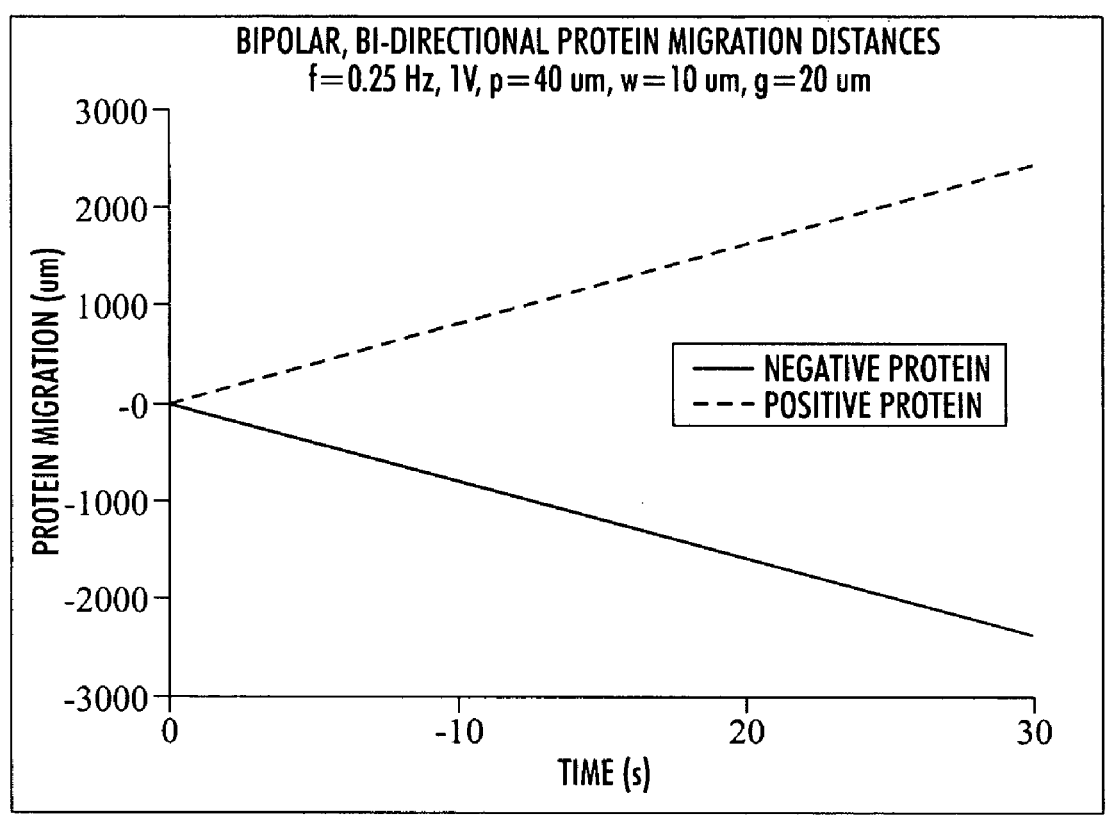
FIG. 29 is a graph of the corresponding migration distances for the positively and negatively charged proteins undergoing bi-directional transport.

The corresponding migration distances are shown in FIG. 29 for the proteins under discussion, i.e. those moving in opposite directions and referred to in FIGS. 26B-28.

Figure 30A:
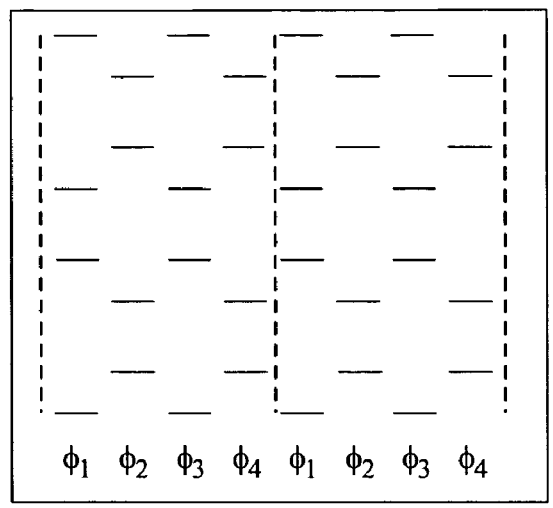
FIG. 30A is a schematic diagram illustrating a spatial voltage distribution on two contiguous four phase electrode groups, for a preferred algorithm.
Figure 30B:
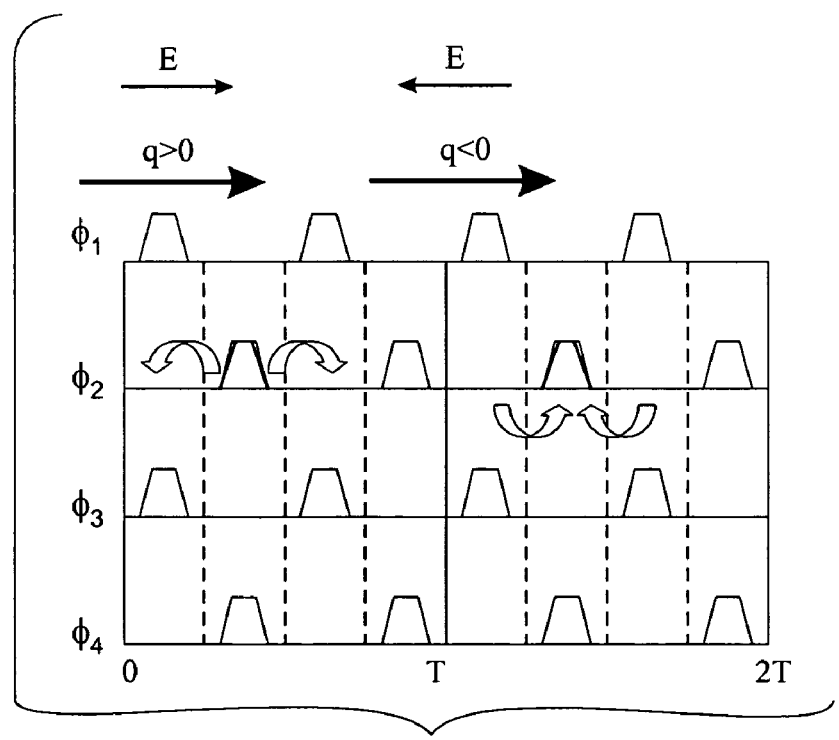
FIG. 30B is a schematic diagram illustrating a temporal voltage distribution for each of the four phases depicted in FIG. 30A and selectively induced stagnation.
Figure 31:
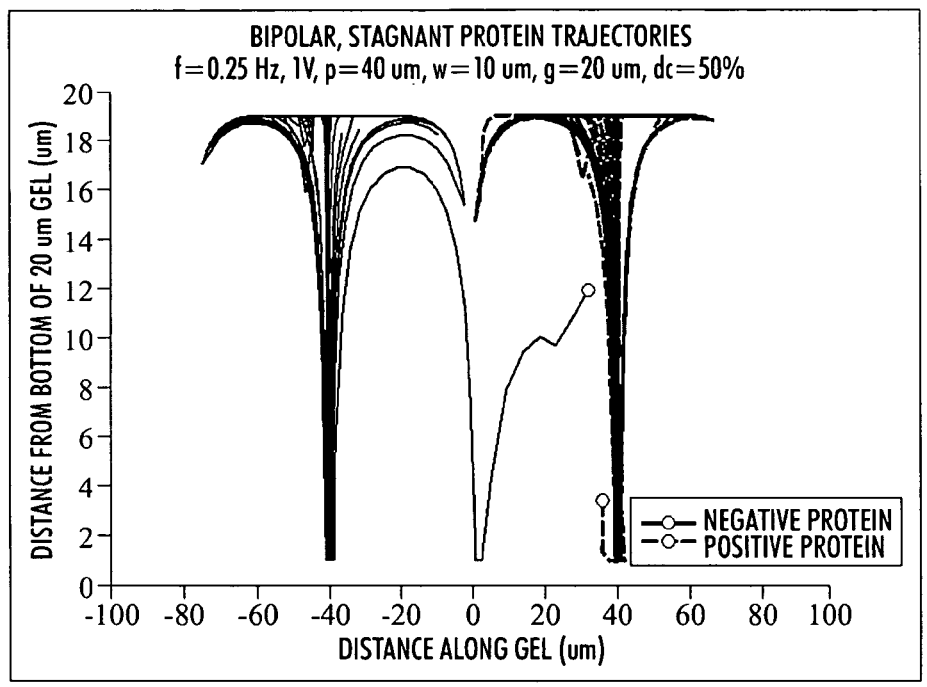
FIG. 31 is a graph of trajectories of a positively charged protein and a negatively charged protein undergoing stagnation as shown in FIG. 30B.

The present discovery also provides an algorithm for interrupting the continuity of the pulse train for both charge species. FIGS. 30A and 30B illustrate an algorithm that leads to stagnation of the transport of proteins or other species. Corresponding trajectories for positively and negatively charged proteins are shown in FIG. 31, where the proteins are trapped within one pitch width of a 4-φ group.

Figure 32:
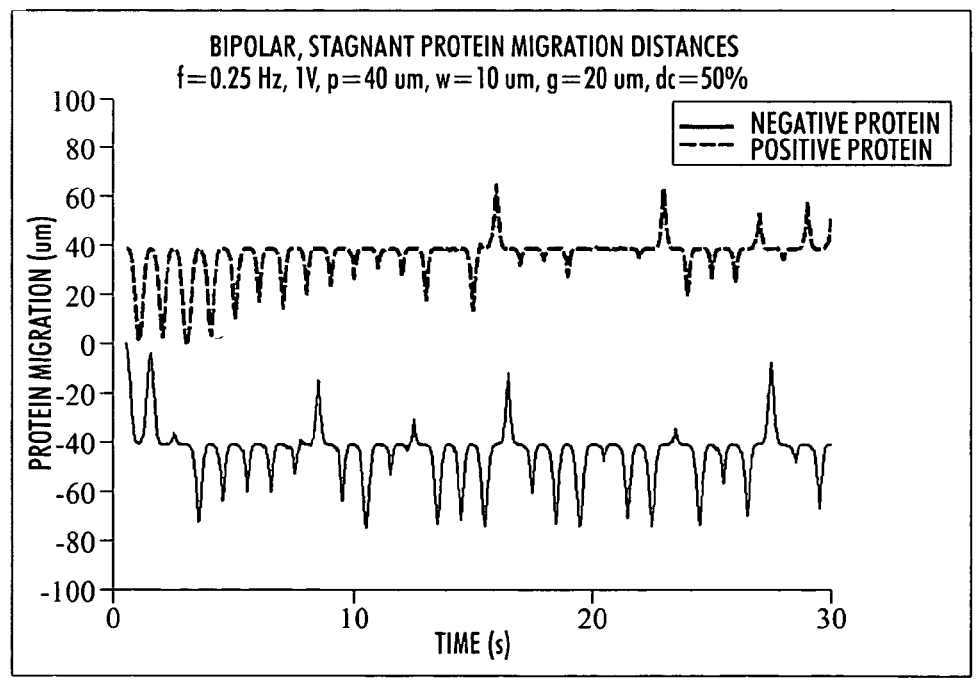
FIG. 32 is a graph of the corresponding migration distances for the positively and negatively charged proteins referenced in FIGS. 30-31.

The migrations depicted in FIG. 32 reveal the back-and-forth motion of the trapped proteins.

The previously described various transport modes achieved by selectively varying a four (4) phase control signal are summarized below in Table 3. It will be appreciated that the various modes of transport may be achieved using different algorithms and a four phase signal, or using algorithms based on signals of different phases.

TABLE 3

Algorithms for Various Transport Modes Using a Four Phase Signal

| Phase | Uni-directional Transport | | | | |
|---|---|---|---|---|---|
| $\phi_1$ | 1 | 0 | 0 | 0 | |
| $\phi_2$ | 0 | 1 | 0 | 0 | |
| $\phi_3$ | 0 | 0 | 1 | 0 | |
| $\phi_4$ | 0 | 0 | 0 | 1 | |
| | 0 | ¼ T | ½ T | ¾ T | T |

| Phase | Bi-directional Transport | | | | |
|---|---|---|---|---|---|
| $\phi_1$ | 1 | 0 | 0 | 0 | |
| $\phi_2$ | 0 | 1 | 0 | 1 | |
| $\phi_3$ | 0 | 0 | 1 | 0 | |
| $\phi_4$ | 0 | 1 | 0 | 1 | |
| | 0 | ¼ T | ½ T | ¾ T | T |

| Phase | No Transport | | | | |
|---|---|---|---|---|---|
| $\phi_1$ | 1 | 0 | 1 | 0 | |
| $\phi_2$ | 0 | 1 | 0 | 1 | |
| $\phi_3$ | 1 | 0 | 1 | 0 | |
| $\phi_4$ | 0 | 1 | 0 | 1 | |
| | 0 | ¼ T | ½ T | ¾ T | T |

Referring to Table 3, a uni-directional mode of transport may be achieved by providing a signal having a first voltage pulse in a first phase of the signal within a first quarter period of the control cycle, a second voltage pulse in a second phase of the signal within a second quarter period of the control cycle, a third voltage pulse in a third phase of the signal within a third quarter period of the control cycle, and a fourth voltage pulse in a fourth phase of the signal within a fourth quarter period of the control cycle. A bi-directional mode of transport may be achieved by providing a control signal having a first voltage pulse in a first phase of the signal within a first quarter period of the control cycle, a second voltage pulse and a third voltage pulse concurrently in a second phase of the signal within a second quarter period of the control cycle, a fourth voltage pulse in a third phase of the signal within a third quarter period of the control cycle, and a fifth voltage pulse and a sixth voltage pulse concurrently in a fourth phase of the signal within a fourth quarter period of the control cycle. And, a mode of no transport or stagnation may be achieved by using a control signal having a first voltage pulse and a second voltage pulse concurrently in a first phase of the signal within a first quarter period of the control cycle, a third voltage pulse and a fourth voltage pulse concurrently in a second phase of the signal within a second quarter period of the control cycle, a fifth voltage pulse and a sixth voltage pulse concurrently in a third phase of the signal within a third quarter period of the control cycle, and a seventh voltage pulse and an eighth voltage pulse concurrently in a fourth phase of the signal within a fourth quarter period of the control cycle.

Although a wide array of configurations, arrangements, and dimensions may be used for the electrodes and electrode grids described herein, several preferred aspects are as follows. The electrode pitch preferably is in the range of from about 600 μm to about 10 μm, and more preferably from about 200 μm to about 40 μm. The spacing between opposing edges of adjacent electrodes is preferably from about 300 μm to about 7.5 μm and more preferably from about 100 μm to about 30 μm. The preferred voltage level applied to the grid and electrodes is from about 5 V to about 0.001 V, and more preferably about 2 V to about 0.10 V. The preferred frequency of the electrical signal depends upon the biomolecules or charged species to be transported, however frequencies in the range of from about 0.001 to about 10 Hz have been found useful, with preferred frequencies being from about 0.020 to about 2 Hz.

A wide array of commercially available electrophoretic equipment may be modified or retrofitted in accordance with the subject matter described herein. Gel electrophoretic systems and cells, IPG strips, power sources, and controllers therefor may be obtained from one or more of the following suppliers: Proteome Systems Limited; Bio-Rad Laboratories; AMRESCO, Inc.; Invitrogen Corp.; Owl Separations Systems; R. Shadel Inc.; Stratagene; Zaxis, Inc.; and Amersham Biosciences.

The present discovery has been described with reference to the preferred embodiments. Obviously, modifications and alterations will occur to others upon reading and understanding the preceding detailed description. It is intended that the present subject matter be construed as including all such modifications and alternations insofar as they come within the scope of the appended claims or the equivalents thereof.

What is claimed is:

1. A traveling wave grid assembly comprising:
   a planar dielectric substrate;
   a plurality of electrically conductive and closely spaced electrodes disposed on said substrate, said electrodes extending parallel to one another and each defining a first end and a second end opposite from said first end;
   a layer of a gel material adapted for retention and migration of biomolecules dispersed therein;
   a voltage controller adapted to provide an electrical signal having a plurality of phases; and
   a plurality of electrically conductive buses providing electrical communication between said controller and said plurality of electrodes, wherein the number of buses corresponds to the number of phases of said electrical signal provided by said controller, and each one of said buses is in electrical communication with both a first end and a second end of a corresponding electrode.

2. The traveling wave grid assembly of claim 1 wherein said plurality of electrodes includes a first electrode, a second electrode adjacent said first electrode, a third electrode adjacent said second electrode, and a fourth electrode adjacent said third electrode, and said plurality of buses includes a first bus in communication with a first end and a second end of said first electrode, a second bus in communication with a first end and a second end of said second electrode, a third bus in communication with a first end and a second end of said third electrode, and a fourth bus in communication with a first end and a second end of said fourth electrode.

3. The traveling wave grid assembly of claim 1 wherein said electrodes comprise copper.

4. The traveling wave grid assembly of claim 1 wherein said electrodes comprise platinum.

5. The traveling wave grid assembly of claim 1 further including a layer of an electrical insulator disposed between said plurality of electrodes and said plurality of buses, wherein said plurality of buses are oriented in said assembly such that they extend across at least a majority of said electrodes.

6. The traveling wave grid assembly of claim 5 wherein said electrical communication between said buses and said electrodes is provided by electrically conductive vias extending through said layer of electrical insulator.

7. The traveling wave grid assembly of claim 6 wherein said vias comprise copper.

8. The traveling wave grid assembly of claim 1 further comprising:
an electrically conductive plane disposed proximate to said plurality of electrodes and oriented such that said plane is generally parallel to said plurality of electrodes and said layer of gel is disposed between said plurality of electrodes and said plane.

9. The traveling wave grid assembly of claim 1 wherein said plurality of buses comprise copper.

10. The traveling wave grid assembly of claim 1 wherein said plurality of buses comprise aluminum.

11. A traveling wave grid module adapted for use in a vertically integrated tiled system including at least another traveling wave grid module, said module comprising;
a planar dielectric substrate;
a plurality of electrically conductive and closely spaced electrodes disposed on said substrate, said electrodes extending parallel to one another and each defining a first end and a second end opposite from said first end;
a set of electrically conductive contact pads accessible along said substrate; and
a plurality of electrically conductive buses providing electrical communication between said plurality of contact pads and said plurality of electrodes, each one of said buses being in electrical communication with a respective electrode.

12. The traveling wave grid module of claim 11 wherein said dielectric substrate includes:
a glass substrate;
a layer of an electrical insulator.

13. The traveling wave grid module of claim 12 wherein said layer of said electrical insulator is disposed between said plurality of electrodes and said plurality of buses.

14. The traveling wave grid module of claim 12 wherein said plurality of buses is disposed between said layer of said electrical insulator and said glass substrate.

15. An electrophoretic cell having a plurality of traveling wave modules, said cell comprising:
a first planar substrate and a second planar substrate spaced from and parallel with said first substrate; and
a plurality of traveling wave modules disposed between said first substrate and said second substrate, each said traveling wave module including (i) a module base, (ii) a plurality of closely spaced electrodes extending across said base, (iii) a plurality of electrically conductive buses in electrical communication with said electrodes, (iv) a plurality of contact pads at which electrical communication to said buses is provided, and (v) a layer of a suitable gel adapted for electrophoresis techniques disposed adjacent said electrodes;
wherein said plurality of traveling wave modules are arranged between said first and second substrates so as to provide at least one column including at least two traveling wave modules, said at least two modules in said column in electrical communication with each other by electrical contact between respective contact pads of said modules in said column.

16. The electrophoretic cell of claim 15 wherein said cell includes 2 to 20 columns of traveling wave modules.

17. The electrophoretic cell of claim 16 wherein each of said columns includes 2 to 10 traveling wave modules.

18. A system for separating, transporting or focusing biomolecules, said system comprising:
a substrate;
a plurality of closely spaced, parallel, electrically conductive electrodes disposed on said substrate;
a layer of a material adapted for the retention and migration of biomolecules disposed therein; and
a voltage controller in electrical communication with said plurality of electrodes, said voltage controller providing a four phase electrical control signal to said plurality of electrodes;
wherein depending upon the signal provided by said voltage controller, a particular mode of transport is imparted to biomolecules disposed in said layer.

19. The system of claim 18 wherein a uni-directional mode of transport is imparted to said biomolecules by said control signal providing: (i) a first voltage pulse in a first phase of said signal within a first quarter period of a control cycle, (ii) a second voltage pulse in a second phase of said signal within a second quarter period of said control cycle, (iii) a third voltage pulse in a third phase of said signal within a third quarter period of said control cycle, and (iv) a fourth voltage pulse in a fourth phase of said signal within a fourth quarter period of said control cycle.

20. The system of claim 18 wherein a bi-directional mode of transport is imparted to said biomolecules by said control signal providing: (i) a first voltage pulse in a first phase of said signal within a first quarter period of a control cycle, (ii) a second voltage pulse and a third voltage pulse concurrently in a second phase of said signal within a second quarter period of said control cycle, (iii) a fourth voltage pulse of said signal within a third quarter period of said control cycle, and (iv) a fifth and a sixth voltage pulse concurrently in a fourth phase of said signal within a fourth quarter period of said control cycle.

21. The system of claim 18 wherein a mode of no transport is imparted to said biomolecules by said control signal providing: (i) a first voltage pulse and a second voltage pulse concurrently in a first phase of said signal within a first quarter period of a control cycle, (ii) a third voltage pulse and a fourth voltage pulse concurrently in a second phase of said signal within a second quarter period of said control cycle, (iii) a fifth voltage pulse and a sixth voltage pulse concurrently in a third phase of said signal within a third quarter period of said control cycle, and (iv) a seventh voltage pulse and an eighth voltage pulse concurrently in a fourth phase of said signal within a fourth quarter period of said control cycle.

22. The system of claim 18 wherein each electrode of said plurality of electrodes defines a first end and a second end opposite from said first end, and said voltage controller provides said control signal to both of said first end and said second end of each electrode of said plurality of electrodes.

23. The system of claim 18 wherein said plurality of electrodes includes a plurality of traveling wave modules, said modules arranged in said system in an array having 2 to 20 columns and each said column having 2 to 10 traveling wave modules.

24. The system of claim 18 wherein said plurality of electrodes generally extend in a plane, said system further comprising:
an electrically conductive plane oriented generally parallel with said plane of electrodes.

* * * * *